(12) United States Patent
Korth et al.

(10) Patent No.: US 7,799,938 B2
(45) Date of Patent: Sep. 21, 2010

(54) METHOD FOR THE PRODUCTION OF (MERCAPTOORGANYL)ALKYL POLYETHER SILANES

(75) Inventors: Karsten Korth, Grenzach-Wyhlen (DE); Dirk Laur, Hausen i.W. (DE); Philipp Albert, Lörrach (DE); Ingo Kiefer, Schwörstadt-Dossenbach (DE)

(73) Assignee: Evonik Degussa GmbH, Essen (DE)

( * ) Notice: Subject to any disclaimer, the term of this patent is extended or adjusted under 35 U.S.C. 154(b) by 0 days.

(21) Appl. No.: 12/213,077

(22) PCT Filed: Nov. 20, 2006

(86) PCT No.: PCT/EP2006/068674

§ 371 (c)(1),
(2), (4) Date: Aug. 26, 2008

(87) PCT Pub. No.: WO2007/068555

PCT Pub. Date: Jun. 21, 2007

(65) Prior Publication Data

US 2008/0319128 A1 Dec. 25, 2008

(30) Foreign Application Priority Data

Dec. 16, 2005 (DE) .................. 10 2005 060 122

(51) Int. Cl.
*C07F 7/18* (2006.01)
*C08K 5/5419* (2006.01)
*C08K 5/548* (2006.01)

(52) U.S. Cl. ..................... 556/429; 524/262

(58) Field of Classification Search ............... 556/429; 524/262
See application file for complete search history.

(56) References Cited

U.S. PATENT DOCUMENTS

| | | |
|---|---|---|
| 3,350,345 A | 10/1967 | Vanderbilt |
| 3,590,065 A | 6/1971 | Rakus |
| 3,842,111 A | 10/1974 | Meyer-Simon |
| 3,873,489 A | 3/1975 | Thurn et al. |
| 3,978,103 A | 8/1976 | Thurn et al. |
| 3,997,356 A | 12/1976 | Thurn |
| 4,048,206 A | 9/1977 | Voronkov |
| 4,076,550 A | 2/1978 | Thurn |
| 4,153,063 A | 5/1979 | Roselius |
| 4,278,587 A | 7/1981 | Wolff et al. |
| 4,456,718 A | 6/1984 | Brinkmann |
| 4,514,231 A | 4/1985 | Kerner |
| 4,551,541 A | 11/1985 | Hanisch |
| 4,629,775 A | 12/1986 | Arai et al. |
| 4,654,368 A | 3/1987 | Sakamoto et al. |
| 4,798,878 A | 1/1989 | Brinkmann |
| 5,107,009 A | 4/1992 | Rauleder |
| 5,637,209 A | 6/1997 | Wright |
| 5,736,484 A | 4/1998 | Polanek |
| 5,780,538 A | 7/1998 | Cohen |
| 5,840,952 A | 11/1998 | Kudo |
| 5,859,275 A | 1/1999 | Munzenberg |
| 5,914,364 A | 6/1999 | Cohen |
| 5,977,225 A | 11/1999 | Scholl |
| 6,133,466 A | 10/2000 | Edelmann |
| 6,140,393 A | 10/2000 | Bomal |
| 6,331,605 B1 | 12/2001 | Lunginsland |
| 6,362,253 B1 | 3/2002 | Durel |
| 6,403,228 B1 | 6/2002 | Mack |
| 6,433,206 B1 | 8/2002 | Gedon |
| 6,465,544 B1 | 10/2002 | Bomal |
| 6,465,672 B2 | 10/2002 | Michel et al. |
| 6,518,335 B2 | 2/2003 | Reedy |
| 6,548,594 B2 | 4/2003 | Luginsland |
| 6,680,398 B1 * | 1/2004 | Boswell et al. ............. 556/429 |
| 6,849,754 B2 | 2/2005 | Deschler |
| 6,893,495 B2 | 5/2005 | Korth |
| 6,995,280 B2 | 2/2006 | Korth |
| 7,019,160 B2 | 3/2006 | Korth |
| 7,186,768 B2 | 3/2007 | Korth |
| 7,332,619 B2 | 2/2008 | Korth |
| 7,339,067 B2 | 3/2008 | Korth |
| 7,384,997 B2 * | 6/2008 | Hasse et al. ................. 524/262 |
| 7,423,165 B2 | 9/2008 | Korth et al. |
| 7,462,221 B2 | 12/2008 | Korth et al. |
| 2003/0083516 A1 | 5/2003 | Korth |
| 2003/0130535 A1 | 7/2003 | Deschler |
| 2003/0200900 A1 | 10/2003 | Korth |
| 2004/0266968 A1 | 12/2004 | Korth |
| 2005/0124740 A1 | 6/2005 | Klockmann |
| 2005/0124821 A1 | 6/2005 | Korth |
| 2005/0124822 A1 | 6/2005 | Korth |
| 2006/0052621 A1 | 3/2006 | Korth |
| 2006/0052622 A1 | 3/2006 | Korth |
| 2006/0161015 A1 | 7/2006 | Klockmann |
| 2006/0204422 A1 | 9/2006 | Korth |
| 2006/0241224 A1 | 10/2006 | Krafczyk |
| 2007/0049669 A1 | 3/2007 | Korth |
| 2007/0066760 A1 | 3/2007 | Korth |
| 2007/0203274 A1 | 8/2007 | Kort |

FOREIGN PATENT DOCUMENTS

| | | |
|---|---|---|
| DE | 915 334 | 7/1954 |
| DE | 2035 619 | 7/1970 |
| DE | 33 14742 A1 | 4/1983 |
| DE | 195 44 469 A1 | 3/1997 |

(Continued)

OTHER PUBLICATIONS

English language abstract for JP 2002-145890, listed as document B1 above.
English language abstract for JP 2005-232445, listed as document B2 above.
International Search Report for PCT/EP2006/068674 filed Nov. 20, 2006.

(Continued)

*Primary Examiner*—Porfirio Nazario Gonzalez
(74) *Attorney, Agent, or Firm*—Law Office of: Michael A. Sanzo, LLC

(57) ABSTRACT

The invention relates to a method for producing (mercaptoorganyl)alkyl polyether silanes by reacting dry mercaptization reagents with a (haloorganyl)alkyl polyether silane.

20 Claims, No Drawings

FOREIGN PATENT DOCUMENTS

| | | |
|---|---|---|
| DE | 196 51 849 A1 | 6/1998 |
| DE | 199 29 021 A1 | 6/1999 |
| DE | 100 40 678 C1 | 8/2000 |
| DE | 101 22 269 A1 | 11/2002 |
| DE | 103 51 735 B3 | 12/2004 |
| EP | 0 085 831 A2 | 8/1983 |
| EP | 0 086 271 A1 | 8/1983 |
| EP | 0 170 865 A1 | 2/1986 |
| EP | 0 323 699 A2 | 7/1989 |
| EP | 0 471 164 A1 | 2/1992 |
| EP | 0 652 245 A2 | 5/1995 |
| EP | 0 700 951 A1 | 3/1996 |
| EP | 0 848 006 A2 | 4/1998 |
| EP | 0 864 608 A1 | 9/1998 |
| EP | 0 949 263 A2 | 10/1999 |
| EP | 0 958 298 B1 | 11/1999 |
| EP | 0 978 525 A2 | 2/2000 |
| EP | 1 002 834 A1 | 5/2000 |
| EP | 1 130 023 A2 | 9/2001 |
| EP | 1 256 604 A2 | 11/2002 |
| EP | 1 285 926 A1 | 2/2003 |
| EP | 1 357 156 A2 | 10/2003 |
| EP | 1 394 167 A1 | 3/2004 |
| EP | 1 529 782 A1 | 5/2005 |
| EP | 1 538 152 A1 | 6/2005 |
| EP | 1 683 801 A2 | 7/2006 |
| EP | 1 700 861 A1 | 9/2006 |
| GB | 1 102 251 | 2/1968 |
| GB | 1 160 644 | 8/1969 |
| GB | 1 310 379 | 3/1973 |
| JP | 62-181346 | 8/1987 |
| JP | 8-291184 | 11/1996 |
| JP | 2002-145890 | 5/2002 |
| JP | 2004-99483 | 4/2004 |
| JP | 2005-47846 | 2/2005 |
| JP | 2005-232445 | 9/2005 |
| WO | WO 99/09036 | 2/1999 |
| WO | WO 02/31040 A2 | 4/2002 |
| WO | WO/2007/085521 A1 | 8/2007 |
| WO | WO/2007/141109 A1 | 12/2007 |

OTHER PUBLICATIONS

Written Opinion of the International Searching Authority for PCT/EP2006/068674 filed Nov. 20, 2006.

International Preliminary Report on Patentability for PCT/EP2006/068674 filed Nov. 20, 2006.

Official Action issued by the German Patent Office for counterpart German application 10 2005 060 122.7.

Dreschler, et al., "3-Chloropropyltrialkoxysilanes: Key Intermediates for the Commercial Production of Organofunctionalized Silanes and Polysiloxanes," *Agnew. Chem. Int. Ed. Engl.* 25:236-252 (1986).

Sorokin, et al., "Synthesis of 1-(Organylthioalkyl)silatranes from 1-(Haloalkyl)silatranes," *J. Gen. Chem.* 69(3):394-398 (1999). Translated from *Zhurnal Obshchei Khimii* 69(3):407-412 (1999).

Sorokin, et al., "S-(Trimethoxysilymethyl)- and S-(Silatranylmethyl)isothiuronium Halides and Their N-Substituted Derivatives," *Russian J. Gen. Chem.* 74(4): 551-558 (2004). Translated from *Zhurnal Obshchei Khimii* 74(4): 603-610 (2004).

Voronkov, et al., 1-[(Acetylthio)alkyl]silatranes, *J. Gen. Chem. USSR* vol. 45(6): 1367 (Dec. 1975). Translated from *Zhurnal Obschei Khimii* 45(6): 1395 (Jun. 1975).

Voronkov, et al., "1-[(Organothio)alkyl]siltranes," *Russian J. Gen. Chem.* 49(3):529-536 (Sep. 1979). Translated from *Zhurnal Obshchei Khimii* 49(3):605-614 (Mar. 1979).

Voronkov, et al., "Photochemical Organothioation of 1-vinysilatrane and its c-methyl Derivatives," *Russian J. Gen. Chem.* 49(6):1130-1136 (Nov. 1979). Translated from *Zhurnal Obshchei Khimii* 49(6):1285-1292 (Jun. 1979).

Voronkov, et al., "O,O-Dialkyl-S-(1-Silatranylalkyl) Dithiophosphates," *Bull. Acad. Sci. USSR Div. Chem. Sci.* 36(8):1745-1747 (1988). Translated from *Izvestiya Akademii Nauk SSSR* 8:1882-1884 (Aug. 1987).

English language abstract for DE 33 14742 A1, cited as reference B2 above.

English language abstract for DE 195 44 469 A1, cited as reference B3 above.

English language abstract for DE 196 51 849 A1, cited as reference B4 above.

English language abstract for DE 199 29 021 A1, cited as reference B5 above.

English language abstract for DE 100 40 678 C1, cited as reference B6 above.

English language abstract for DE 101 22 269 A1, cited as reference B7 above.

English language abstract for DE 103 51 735 B3, cited as reference B8 above.

English language abstract for EP 0 848 006 A2, cited as reference B16 above.

English language abstract for EP 0 978 525 A2, cited as reference B19 above.

English language abstract for EP 1 130 023 A2, cited as reference B21 above.

English language abstract for EP 1 256 604 A2, cited as reference B22 above.

English language abstract for EP 1 357 156 A2, cited as reference B24 above.

English language abstract for JP 62-181346, cited as reference B31 above.

English language abstract for JP 8-291184, cited as reference B32 above.

English language abstract for JP 2004-099483, cited as reference B33 above.

English language abstract for JP 2005-047846, cited as reference B34 above.

English translation of the International Preliminary Report on Patentability for PCT/EP2006/068674 filed Nov. 20, 2006.

English translation of the Written Opinion of the International Searching Authority for PCT/EP2006/068674 filed Nov. 20, 2006.

English language abstract for EP 1 394 167, cited as document B2 above.

English translation for WO/2007/141109, cited as document B5 above.

* cited by examiner

METHOD FOR THE PRODUCTION OF (MERCAPTOORGANYL)ALKYL POLYETHER SILANES

CROSS REFERENCE TO RELATED APPLICATIONS

The present application is US national stage of international application PCT/EP2006/068674, which had an international filing date of Nov. 20, 2006, and which was published in German under PCT Article 21(2) on Jun. 21, 2007. The international application claims priority to German application 10 2005 060 122.7, filed on Dec. 16, 2005. These prior applications are hereby incorporated by reference in their entirety.

The invention relates to a process for preparing (mercaptoorganyl)alkyl polyether silanes.

EP 1285926 discloses the preparation of organosilicon compounds of the formulae $(R^1O)_2 (R^2O)Si—R^3—Y_m$ and $(R^1O) (R^2O)_2Si—R^3—Y_m$ by reacting silanes of the general formula $(R^1O)_3Si—R^3—Y_m$ with alkyl polyether alcohols $R^2OH$.

JP 62-181346 discloses the preparation of (mercaptoorganyl)alkyl polyether silanes from (mercaptoorganyl)alkoxysilanes by transesterification with alkyl polyether alcohols.

Additionally known from EP 1529782 and EP 1538152 are processes for preparing (mercaptoorganyl)alkoxysilanes, wherein alkali metal sulfide or alkali metal hydrogensulfide is reacted with a mixture of (haloorganyl)alkoxysilane and (haloorganyl)halosilane in alcohol with exclusion of air.

JP 3091993, JP 2005-047846, JP 2004-099483 and U.S. Pat. No. 5,840,952 disclose processes for preparing mercaptopropylsilanes of the formula $HS—(CH_2)_3—Si(R^1)_n(OR^2)_{3-n}$ by reacting halopropylsilanes of the formula $Y—(CH_2)_3—Si(R^1)_n(OR^2)_{3-n}$ with alkali metal hydrogensulfide.

DE 102005032658.7 discloses a process for preparing mercaptosilanes, wherein silanes of the general formula

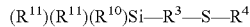

are reacted in a catalyzed reaction with an alkoxylated alcohol $R^1—H$ with elimination of $R^7—OH$, and $R^7—OH$ is removed from the reaction mixture.

DE 102005052233 discloses a process for preparing organosilanes of the general formula $[R_2(R'O)Si—R''-]_nA_m$ by reacting (haloorganyl)alkoxysilanes with water-containing sulfuration reagents.

Disadvantages of the known processes are the long reaction times and low conversions or low space-time yields with good selectivity.

It is an object of the invention to provide a process for preparing (mercaptoorganyl)alkyl polyether silanes, which enables short reaction times with high conversions or high space-time yields with good selectivity in the conversion of the starting materials.

The invention provides a process for preparing (mercaptoorganyl)alkyl polyether silanes, which is characterized in that a dry mercaptation reagent having a water content of less than 3% by weight is reacted with a (haloorganyl)alkyl polyether silane.

The reaction can be carried out with exclusion of air. The reaction can be carried out in a closed vessel.

The reaction can be carried out in a solvent or without solvent.

(Mercaptoorganyl)alkyl polyether silanes may be compounds of the general formula I

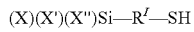

where

X is an alkyl polyether group $O—((CR^{II}_2)_w—O—)_v$Alk, preferably $O—(CH_2—CH_2—O—)_u$Alk or $O—(CH(CH_3)—CH_2—O—)_r$Alk, where v=1-40, preferably 2-30, more preferably 3-25, even more preferably 4-20, exceptionally preferably 6-16, w=1-40, preferably 2-30, more preferably 2-20, even more preferably 3-10, u=1-40, preferably 2-30, more preferably 3-25, even more preferably 4-20, exceptionally preferably 6-16, r=1-40, preferably 2-30, more preferably 3-25, even more preferably 4-20, exceptionally preferably 6-16, $R^{II}$ are each independently H, a phenyl group or an alkyl group, preferably a $C_1$-$C_{11}$-alkyl group, more preferably a $CH_3$— or $CH_2—CH_3$— group, Alk is a branched or unbranched, saturated or unsaturated, substituted or unsubstituted, aliphatic, aromatic or mixed aliphatic/aromatic monovalent $C_1$-$C_{35}$-hydrocarbon group, preferably $C_2$-$C_{25}$-hydrocarbon group, more preferably $C_3$-$C_{20}$-hydrocarbon group, even more preferably $C_6$-$C_{18}$-hydrocarbon group, exceptionally preferably $C_{11}$-$C_{18}$-hydrocarbon group, X' is an unbranched or branched alkyl, preferably $C_1$-$C_{18}$-alkyl, more preferably $CH_3$, $CH_2—CH_3$, $CH(CH_3)—CH_3$, $CH_2—CH_2—CH_3$ or $C_4$-$C_{18}$-alkyl, a branched or unbranched alkoxy, preferably $C_1$-$C_{18}$-alkoxy, more preferably —$OCH_3$, —$OCH_2—CH_3$, —$OCH(CH_3)—CH_3$, —$OCH_2—CH_2—CH_3$, —$OC_{12}H_{25}$, —$OC_{13}H_{27}$, —$OC_{14}H_{29}$ or $C_{15}$-$C_{18}$-alkoxy, a branched or unbranched $C_2$-$C_{25}$-alkenyloxy, preferably $C_4$-$C_{20}$-alkenyloxy, more preferably $C_6$- to $C_{18}$-alkenyloxy, a $C_6$-$C_{35}$-aryloxy, preferably $C_9$-$C_{30}$-aryloxy, more preferably phenyloxy (—$OC_6H_5$) or $C_9$- to $C_{18}$-aryloxy, a branched or unbranched $C_7$-$C_{35}$-alkylaryloxy group, preferably $C_9$-$C_{30}$-alkylaryloxy group, more preferably benzyloxy, (—O—$CH_2$—$C_6H_5$) or —O—$CH_2$—$CH_2$—$C_6H_5$, a branched or unbranched $C_7$-$C_{35}$-aralkyloxy group, preferably $C_9$-$C_{25}$-aralkyloxy group, more preferably tolyloxy (—O—$C_6H_4$—$CH_3$) or a $C_9$- to $C_{18}$-aralkyloxy group, or an X, X" is a branched or unbranched alkyl, preferably $C_1$-$C_{18}$-alkyl, more preferably $CH_3$, $CH_2—CH_3$, $CH(CH_3)—CH_3$, $CH_2—CH_2—CH_3$ or $C_4$-$C_{18}$-alkyl, a branched or unbranched alkoxy, preferably $C_1$-$C_{18}$-alkoxy, more preferably —$OCH_3$, —$OCH_2—CH_3$, —$OCH(CH_3)—CH_3$, —$OCH_2—CH_2—CH_3$, —$OC_{12}H_{25}$, —$OC_{13}H_{27}$, —$OC_{14}H_{29}$ or $C_{15}$-$C_{18}$-alkoxy, a branched or unbranched $C_2$-$C_{25}$-alkenyloxy group, preferably $C_4$-$C_{20}$-alkenyloxy, more preferably $C_6$- to $C_{18}$-alkenyloxy, a $C_6$-$C_{35}$-aryloxy group, preferably $C_9$-$C_{30}$-aryloxy, more preferably phenyloxy (—$OC_6H_5$) or $C_9$- to $C_{18}$-aryloxy, a branched or unbranched $C_7$-$C_{35}$-alkylaryloxy group, preferably $C_9$-$C_{30}$-alkylaryloxy group, more preferably benzyloxy, (—O—$CH_2$—$C_6H_5$) or —O—$CH_2$—$CH_2$—$C_6H_5$, a branched or unbranched $C_7$-$C_{35}$-aralkyloxy group, preferably $C_9$-$C_{25}$-aralkyloxy group, more preferably tolyloxy (—O—$C_6H_4$—$CH_3$) or a $C_9$- to $C_{18}$-aralkyloxy group, or an X, $R^I$ is a branched or unbranched, saturated or unsaturated, aliphatic, aromatic or mixed aliphatic/aromatic divalent $C_1$-$C_{30}$-hydrocarbon group which is optionally substituted.

It is possible in the process according to the invention for preparing (mercaptoorganyl)alkyl polyether silanes for compounds of the general formula I or else mixtures of compounds of the general formula I to form.

It is possible in the process according to the invention, through hydrolysis and condensation of the compounds of the general formula I, for their oligomers to form as by-products. $R^I$ may be —$CH_2$—, —$CH_2CH_2$—, —$CH_2CH_2CH_2$—, —$CH_2CH_2CH_2CH_2$—, —$CH(CH_3)$—, —$CH_2CH(CH_3)$—, —$CH(CH_3)CH_2$—, —$C(CH_3)_2$—, —$CH(C_2H_5)$—, —$CH_2CH_2CH(CH_3)$—, —$CH_2CH(CH_3)CH_2CH_2$—, —$CH_2CH(CH_3)CH_2$—, —$CH_2CH_2CH_2CH_2CH_2$—, —$CH_2CH_2CH_2CH_2CH_2$—, —$CH_2CH_2CH_2CH_2CH_2CH_2CH_2$—, —$CH_2CH_2CH_2CH_2CH_2CH_2CH_2CH_2$—, —$CH_2CH_2CH_2CH_2CH_2CH_2CH_2CH_2CH_2$—, —$CH_2CH_2CH_2CH_2CH_2CH_2CH_2CH_2CH_2CH_2$—, —$CH_2CH_2CH_2CH_2CH_2CH_2CH_2CH_2CH_2CH_2CH_2$—, —$CH_2CH_2CH_2CH_2CH_2CH_2CH_2CH_2CH_2CH_2CH_2CH_2$—, —$CH_2CH_2CH_2CH_2CH_2CH_2CH_2CH_2CH_2CH_2CH_2CH_2CH_2$—, —$CH_2CH_2CH_2CH_2CH_2CH_2CH_2CH_2CH_2CH_2CH_2CH_2CH_2CH_2$— or 

The alkyl polyether group O—(($CR^{II}_2$)$_w$—O—)$_v$-Alk may be O—($CR^{II}_2$—$CR^{II}_2$—O)$_v$-Alk.

The ($CR^{II}_2$—$CR^{II}_2$—O)$_v$-Alk group may preferably contain ethylene oxide units, ($CH_2$—$CH_2$—O)$_v$-Alk, propylene oxide units ($CH(CH_3)$—$CH_2$—O)$_v$-Alk or ($CH_2$—$CH(CH_3)$)$_2$—O)$_v$-Alk, or butylene oxide units, for example (—$CH(CH_2$—$CH_3)$—$CH_2$—O)$_v$-Alk, or (—$CH_2$—$CH(CH_2$—$CH_3)$—O)$_v$-Alk.

The alkyl polyether group O—($CR^{II}_2$—$CR^{II}_2$—O)$_v$-Alk may be O—($CH_2$—$CH_2$O)—$C_4H_9$, O—($CH_2$—$CH_2$O)$_2$—$C_4H_9$, O—($CH_2$—$CH_2$O)$_3$—$C_4H_9$, O—($CH_2$—$CH_2$O)$_4$—$C_4H_9$, O—($CH_2$—$CH_2$O)$_5$—$C_4H_9$, O—($CH_2$—$CH_2$O)$_6$—$C_4H_9$, O—($CH_2$—$CH_2$O)$_7$—$C_4H_9$, O—($CH(CH_3)$—$CH_2$O)—$C_4H_9$, O—($CH(CH_3)$—$CH_2$O)$_2$—$C_4H_9$, O—($CH(CH_3)$—$CH_2$O)$_3$—$C_4H_9$, O—($CH(CH_3)$—$CH_2$O)$_4$—$C_4H_9$, O—($CH(CH_3)$—$CH_2$O)$_5$—$C_4H_9$, O—($CH(CH_3)$—$CH_2$O)$_6$—$C_4H_9$, O—($CH(CH_3)$—$CH_2$O)$_7$—$C_4H_9$, O—($CH_2$—$CH_2$O)—$C_5H_{11}$, O—($CH_2$—$CH_2$O)$_2$—$C_5H_{11}$, O—($CH_2$—$CH_2$O)$_3$—$C_5H_{11}$, O—($CH_2$—$CH_2$O)$_4$—$C_5H_{11}$, O—($CH_2$—$CH_2$O)$_5$—$C_5H_{11}$, O—($CH_2$—$CH_2$O)$_6$—$C_5H_{11}$, O—($CH_2$—$CH_2$O)$_7$—$C_5H_{11}$, O—($CH(CH_3)$—$CH_2$O)—$C_5H_{11}$, O—($CH(CH_3)$—$CH_2$O)$_2$—$C_5H_{11}$, O—($CH(CH_3)$—$CH_2$O)$_3$—$C_5H_{11}$, O—($CH(CH_3)$—$CH_2$O)$_4$—$C_5H_{11}$, O—($CH(CH_3)$—$CH_2$O)$_5$—$C_5H_{11}$, O—($CH(CH_3)$—$CH_2$O)$_6$—$C_5H_{11}$, O—($CH(CH_3)$—$CH_2$O)$_7$—$C_5H_{11}$, O—($CH_2$—$CH_2$O)—$C_6H_{13}$, O—($CH_2$—$CH_2$O)$_2$—$C_6H_{13}$, O—($CH_2$—$CH_2$O)$_3$—$C_6H_{13}$, O—($CH_2$—$CH_2$O)$_4$—$C_6H_{13}$, O—($CH_2$—$CH_2$O)$_5$—$C_6H_{13}$, O—($CH_2$—$CH_2$O)$_6$—$C_6H_{13}$, O—($CH_2$—$CH_2$O)$_7$—$C_6H_{13}$, O—($CH(CH_3)$—$CH_2$O)—$C_6H_{13}$, O—($CH(CH_3)$—$CH_2$O)$_2$—$C_6H_{13}$, O—($CH(CH_3)$—$CH_2$O)$_3$—$C_6H_{13}$, O—($CH(CH_3)$—$CH_2$O)$_4$—$C_6H_{13}$, O—($CH(CH_3)$—$CH_2$O)$_5$—$C_6H_{13}$, O—($CH(CH_3)$—$CH_2$O)$_6$—$C_6H_{13}$, O—($CH(CH_3)$—$CH_2$O)$_7$—$C_6H_{13}$, O—($CH_2$—$CH_2$O)—$C_7H_{15}$, O—($CH_2$—$CH_2$O)$_2$—$C_7H_{15}$, O—($CH_2$—$CH_2$O)$_3$—$C_7H_{15}$, O—($CH_2$—$CH_2$O)$_4$—$C_7H_{15}$, O—($CH_2$—$CH_2$O)$_5$—$C_7H_{15}$, O—($CH_2$—$CH_2$O)$_6$—$C_7H_{15}$, O—($CH_2$—$CH_2$O)$_7$—$C_7H_{15}$, O—($CH(CH_3)$—$CH_2$O)—$C_7H_{15}$, O—($CH(CH_3)$—$CH_2$O)$_2$—$C_7H_{15}$, O—($CH(CH_3)$—$CH_2$O)$_3$—$C_7H_{15}$, O—($CH(CH_3)$—$CH_2$O)$_4$—$C_7H_{15}$, O—($CH(CH_3)$—$CH_2$O)$_5$—$C_7H_{15}$, O—($CH(CH_3)$—$CH_2$O)$_6$—$C_7H_{15}$, O—($CH(CH_3)$—$CH_2$O)$_7$—$C_7H_{15}$, O—($CH_2$—$CH_2$O)—$C_8H_{17}$, O—($CH_2$—$CH_2$O)$_2$—$C_8H_{17}$, O—($CH_2$—$CH_2$O)$_3$—$C_8H_{17}$, O—($CH_2$—$CH_2$O)$_4$—$C_8H_{17}$, O—($CH_2$—$CH_2$O)$_5$—$C_8H_{17}$, O—($CH_2$—$CH_2$O)$_6$—$C_8H_{17}$, O—($CH_2$—$CH_2$O)$_7$—$C_8H_{17}$, O—($CH(CH_3)$—$CH_2$O)—$C_8H_{17}$, O—($CH(CH_3)$—$CH_2$O)$_2$—$C_8H_{17}$, O—($CH(CH_3)$—$CH_2$O)$_3$—$C_8H_{17}$, O—($CH(CH_3)$—$CH_2$O)$_4$—$C_8H_{17}$, O—($CH(CH_3)$—$CH_2$O)$_5$—$C_8H_{17}$, O—($CH(CH_3)$—$CH_2$O)$_6$—$C_8H_{17}$, O—($CH(CH_3)$—$CH_2$O)$_7$—$C_8H_{17}$, O—($CH_2$—$CH_2$O)—$C_9H_{19}$, O—($CH_2$—$CH_2$O)$_2$—$C_9H_{19}$, O—($CH_2$—$CH_2$O)$_3$—$C_9H_{19}$, O—($CH_2$—$CH_2$O)$_4$—$C_9H_{19}$, O—($CH_2$—$CH_2$O)$_5$—$C_9H_{19}$, O—($CH_2$—$CH_2$O)$_6$—$C_9H_{19}$, O—($CH_2$—$CH_2$O)$_7$—$C_9H_{19}$, O—($CH(CH_3)$—$CH_2$O)—$C_9H_{19}$, O—($CH(CH_3)$—$CH_2$O)$_2$—$C_9H_{19}$, O—($CH(CH_3)$—$CH_2$O)$_3$—$C_9H_{19}$, O—($CH(CH_3)$—$CH_2$O)$_4$—$C_9H_{19}$, O—($CH(CH_3)$—$CH_2$O)$_5$—$C_9H_{19}$, O—($CH(CH_3)$—$CH_2$O)$_6$—$C_9H_{19}$, O—($CH(CH_3)$—$CH_2$O)$_7$—$C_9H_{19}$, O—($CH_2$—$CH_2$O)—$C_{10}H_{21}$, O—($CH_2$—$CH_2$O)$_2$—$C_{10}H_{21}$, O—($CH_2$—$CH_2$O)$_3$—$C_{10}H_{21}$, O—($CH_2$—$CH_2$O)$_4$—$C_{10}H_{21}$, O—($CH_2$—$CH_2$O)$_5$—$C_{10}H_{21}$, O—($CH_2$—$CH_2$O)$_6$—$C_{10}H_{21}$, O—($CH_2$—$CH_2$O)$_7$—$C_{10}H_{21}$, O—($CH(CH_3)$—$CH_2$O)—$C_{10}H_{21}$, O—($CH(CH_3)$—$CH_2$O)$_2$—$C_{10}H_{21}$, O—($CH(CH_3)$—$CH_2$O)$_3$—$C_{10}H_{21}$, O—($CH(CH_3)$—$CH_2$O)$_4$—$C_{10}H_{21}$, O—($CH(CH_3)$—$CH_2$O)$_5$—$C_{10}H_{21}$, O—($CH(CH_3)$—$CH_2$O)$_6$—$C_{10}H_{21}$, O—($CH(CH_3)$—$CH_2$O)$_7$—$C_{10}H_{21}$, O—($CH_2$—$CH_2$O)—$C_{11}H_{23}$, O—($CH_2$—$CH_2$O)$_2$—$C_{11}H_{23}$, O—($CH_2$—$CH_2$O)$_3$—$C_{11}H_{23}$, O—($CH_2$—$CH_2$O)$_4$—$C_{11}H_{23}$, O—($CH_2$—$CH_2$O)$_5$—$C_{11}H_{23}$, O—($CH_2$—$CH_2$O)$_6$—$C_{11}H_{23}$, O—($CH_2$—$CH_2$O)$_7$—$C_{11}H_{23}$, O—($CH(CH_3)$—$CH_2$O)—$C_{11}H_{23}$, O—($CH(CH_3)$—$CH_2$O)$_2$—$C_{11}H_{23}$, O—($CH(CH_3)$—$CH_2$O)$_3$—$C_{11}H_{23}$, O—($CH(CH_3)$—$CH_2$O)$_4$—$C_{11}H_{23}$, O—($CH(CH_3)$—$CH_2$O)$_5$—$C_{11}H_{23}$, O—($CH(CH_3)$—$CH_2$O)$_6$—$C_{11}H_{23}$, O—($CH(CH_3)$—$CH_2$O)$_7$—$C_{11}H_{23}$, O—($CH_2$—$CH_2$O)—$C_{12}H_{25}$, O—($CH_2$—$CH_2$O)$_2$—$C_{12}H_{25}$, O—($CH_2$—$CH_2$O)$_3$—$C_{12}H_{25}$, O—($CH_2$—$CH_2$O)$_4$—$C_{12}H_{25}$, O—($CH_2$—$CH_2$O)$_5$—$C_{12}H_{25}$, O—($CH_2$—$CH_2$O)$_6$—$C_{12}H_{25}$, O—($CH_2$—$CH_2$O)$_7$—$C_{12}H_{25}$, O—($CH(CH_3)$—$CH_2$O)—$C_{12}H_{25}$, O—($CH(CH_3)$—$CH_2$O)$_2$—$C_{12}H_{25}$, O—($CH(CH_3)$—$CH_2$O)$_3$—$C_{12}H_{25}$, O—($CH(CH_3)$—$CH_2$O)$_4$—$C_{12}H_{25}$, O—($CH(CH_3)$—$CH_2$O)$_5$—$C_{12}H_{25}$, O—($CH(CH_3)$—$CH_2$O)$_6$—$C_{12}H_{25}$, O—($CH(CH_3)$—$CH_2$O)$_7$—$C_{12}H_{25}$, O—(CH$_2$—CH$_2$O)—C$_{13}$H$_{27}$, O—(CH$_2$—CH$_2$O)$_2$—C$_{13}$H$_{27}$, O—(CH$_2$—CH$_2$O)$_3$—C$_{13}$H$_{27}$, O—(CH$_2$—CH$_2$O)$_4$—C$_{13}$H$_{27}$, O—(CH$_2$—CH$_2$O)$_5$—C$_{13}$H$_{27}$, O—(CH$_2$—CH$_2$O)$_6$—C$_{13}$H$_{27}$, O—(CH$_2$—CH$_2$O)$_7$—C$_{13}$H$_{27}$, O—(CH(CH$_3$)—CH$_2$O)—C$_{13}$H$_{27}$, O—(CH(CH$_3$)—CH$_2$O)$_2$—C$_{13}$H$_{27}$, O—(CH(CH$_3$)—CH$_2$O)$_3$—C$_{13}$H$_{27}$, O—(CH(CH$_3$)—CH$_2$O)$_4$—C$_{13}$H$_{27}$, O—(CH(CH$_3$)—CH$_2$O)$_5$—C$_{13}$H$_{27}$, O—(CH(CH$_3$)—CH$_2$O)$_6$—C$_{13}$H$_{27}$, O—(CH(CH$_3$)—CH$_2$O)$_7$—C$_{13}$H$_{27}$, O—(CH$_2$—CH$_2$O)—C$_{14}$H$_{29}$, O—(CH$_2$—CH$_2$O)$_2$—C$_{14}$H$_{29}$, O—(CH$_2$—CH$_2$O)$_3$—C$_{14}$H$_{29}$, O—(CH$_2$—CH$_2$O)$_4$—C$_{14}$H$_{29}$, O—(CH$_2$—CH$_2$O)$_5$—C$_{14}$H$_{29}$, O—(CH$_2$—CH$_2$O)$_6$—C$_{14}$H$_{29}$, O—(CH$_2$—CH$_2$O)$_7$—C$_{14}$H$_{29}$, O—(CH(CH$_3$)—CH$_2$O)—C$_{14}$H$_{29}$, O—(CH(CH$_3$)—CH$_2$O)$_2$—C$_{14}$H$_{29}$, O—(CH(CH$_3$)—CH$_2$O)$_3$—C$_{14}$H$_{29}$, O—(CH(CH$_3$)—CH$_2$O)$_4$—C$_{14}$H$_{29}$, O—(CH(CH$_3$)—CH$_2$O)$_5$—C$_{14}$H$_{29}$, O—(CH(CH$_3$)—CH$_2$O)$_6$—C$_{14}$H$_{29}$, O—(CH(CH$_3$)—CH$_2$O)$_7$—C$_{14}$H$_{29}$, O—(CH$_2$—CH$_2$O)—C$_{15}$H$_{31}$, O—(CH$_2$—CH$_2$O)$_2$—C$_{15}$H$_{31}$, O—(CH$_2$—CH$_2$O)$_3$—C$_{15}$H$_{31}$, O—(CH$_2$—CH$_2$O)$_4$—C$_{15}$H$_{31}$, O—(CH$_2$—CH$_2$O)$_5$—C$_{15}$H$_{31}$, O—(CH$_2$—CH$_2$O)$_6$—C$_{15}$H$_{31}$, O—(CH$_2$—CH$_2$O)$_7$—C$_{15}$H$_{31}$, O—(CH(CH$_3$)—CH$_2$O)—C$_{15}$H$_{31}$, O—(CH(CH$_3$)—CH$_2$O)$_2$—C$_{15}$H$_{31}$, O—(CH(CH$_3$)—CH$_2$O)$_3$—C$_{15}$H$_{31}$, O—(CH(CH$_3$)—CH$_2$O)$_4$—C$_{15}$H$_{31}$, O—(CH(CH$_3$)—CH$_2$O)$_5$—C$_{15}$H$_{31}$, O—(CH(CH$_3$)—CH$_2$O)$_6$—C$_{15}$H$_{31}$, O—(CH(CH$_3$)—CH$_2$O)$_7$—C$_{15}$H$_{31}$, O—(CH$_2$—CH$_2$O)—C$_{16}$H$_{33}$, O—(CH$_2$—CH$_2$O)$_2$—C$_{16}$H$_{33}$, O—(CH$_2$—CH$_2$O)$_3$—C$_{16}$H$_{33}$, O—(CH$_2$—CH$_2$O)$_4$—C$_{16}$H$_{33}$, O—(CH$_2$—CH$_2$O)$_5$—C$_{16}$H$_{33}$, O—(CH$_2$—CH$_2$O)$_6$—C$_{16}$H$_{33}$, O—(CH$_2$—CH$_2$O)$_7$—C$_{16}$H$_{33}$, O—(CH(CH$_3$)—CH$_2$O)—C$_{16}$H$_{33}$, O—(CH(CH$_3$)—CH$_2$O)$_2$—C$_{16}$H$_{33}$, O—(CH(CH$_3$)—CH$_2$O)$_3$—C$_{16}$H$_{33}$, O—(CH(CH$_3$)—CH$_2$O)$_4$—C$_{16}$H$_{33}$, O—(CH(CH$_3$)—CH$_2$O)$_5$—C$_{16}$H$_{33}$, O—(CH(CH$_3$)—CH$_2$O)$_6$—C$_{16}$H$_{33}$, O—(CH(CH$_3$)—CH$_2$O)$_7$—C$_{16}$H$_{33}$, O—(CH$_2$—CH$_2$O)—C$_{17}$H$_{35}$, O—(CH$_2$—CH$_2$O)$_2$—C$_{17}$H$_{35}$, O—(CH$_2$—CH$_2$O)$_3$—C$_{17}$H$_{35}$, O—(CH$_2$—CH$_2$O)$_4$—C$_{17}$H$_{35}$, O—(CH$_2$—CH$_2$O)$_5$—C$_{17}$H$_{35}$, O—(CH$_2$—CH$_2$O)$_6$—C$_{17}$H$_{35}$, O—(CH$_2$—CH$_2$O)$_7$—C$_{17}$H$_{35}$, O—(CH(CH$_3$)—CH$_2$O)—C$_{17}$H$_{35}$, O—(CH(CH$_3$)—CH$_2$O)$_2$—C$_{17}$H$_{35}$, O—(CH(CH$_3$)—CH$_2$O)$_3$—C$_{17}$H$_{35}$, O—(CH(CH$_3$)—CH$_2$O)$_4$—C$_{17}$H$_{35}$, O—(CH(CH$_3$)—CH$_2$O)$_5$—C$_{17}$H$_{35}$, O—(CH(CH$_3$)—CH$_2$O)$_6$—C$_{17}$H$_{35}$, O—(CH(CH$_3$)—CH$_2$O)$_7$—C$_{17}$H$_{35}$, O—(CH$_2$—CH$_2$O)—C$_{18}$H$_{37}$, O—(CH$_2$—CH$_2$O)$_2$—C$_{18}$H$_{37}$, O—(CH$_2$—CH$_2$O)$_3$—C$_{18}$H$_{37}$, O—(CH$_2$—CH$_2$O)$_4$—C$_{18}$H$_{37}$, O—(CH$_2$—CH$_2$O)$_5$—C$_{18}$H$_{37}$, O—(CH$_2$—CH$_2$O)$_6$—C$_{18}$H$_{37}$, O—(CH$_2$—CH$_2$O)$_7$—C$_{18}$H$_{37}$, O—(CH(CH$_3$)—CH$_2$O)—C$_{18}$H$_{37}$, O—(CH(CH$_3$)—CH$_2$O)$_2$—C$_{18}$H$_{37}$, O—(CH(CH$_3$)—CH$_2$O)$_3$—C$_{18}$H$_{37}$, O—(CH(CH$_3$)—CH$_2$O)$_4$—C$_{18}$H$_{37}$, O—(CH(CH$_3$)—CH$_2$O)$_5$—C$_{18}$H$_{37}$, O—(CH(CH$_3$)—CH$_2$O)$_6$—C$_{18}$H$_{37}$, O—(CH(CH$_3$)—CH$_2$O)$_7$—C$_{18}$H$_{37}$, O—(CH$_2$—CH$_2$O)—C$_6$H$_4$—C$_9$H$_{19}$, O—(CH$_2$—CH$_2$O)$_2$—C$_6$H$_4$—C$_9$H$_{19}$, O—(CH$_2$—CH$_2$O)$_3$—C$_6$H$_4$—C$_9$H$_{19}$, O—(CH$_2$—CH$_2$O)$_4$—C$_6$H$_4$—C$_9$H$_{19}$, O—(CH$_2$—CH$_2$O)$_5$—C$_6$H$_4$—C$_9$H$_{19}$, O—(CH$_2$—CH$_2$O)$_6$—C$_6$H$_4$—C$_9$H$_{19}$, O—(CH$_2$—CH$_2$O)$_7$—C$_6$H$_4$—C$_9$H$_{19}$, O—(CH(CH$_3$)—CH$_2$O)—C$_6$H$_4$—C$_9$H$_{19}$, O—(CH(CH$_3$)—CH$_2$O)$_2$—C$_6$H$_4$—C$_9$H$_{19}$, O—(CH(CH$_3$)—CH$_2$O)$_3$—C$_6$H$_4$—C$_9$H$_{19}$, O—(CH(CH$_3$)—CH$_2$O)$_4$—C$_6$H$_4$—C$_9$H$_{19}$, O—(CH(CH$_3$)—CH$_2$O)$_5$—C$_6$H$_4$—C$_9$H$_{19}$, O—(CH(CH$_3$)—CH$_2$O)$_6$—C$_6$H$_4$—C$_9$H$_{19}$ or O—(CH(CH$_3$)—CH$_2$O)$_7$—C$_6$H$_4$—C$_9$H$_{19}$, where the hydrocarbon chains may be branched or unbranched.

The alkyl polyether group O—((CR$^{II}_2$)$_w$—O—)$_v$Alk cannot be an —O—CH$_2$—CH$_2$O—CH$_3$— group.

The alkyl polyether group X as O—((CR$^{II}_2$)$_w$—O—)$_v$Alk may contain more than 6, preferably more than 8, more preferably more than 10, carbon atoms.

The alkyl polyether group X as O—((CH$_2$—CH$_2$—O—)$_u$-Alk may contain more than 6, preferably more than 8, more preferably more than 10, carbon atoms.

The alkyl polyether group X as O—((CH$_2$—CH$_2$—O—)$_r$-Alk may contain more than 7, preferably more than 10, more preferably more than 12, carbon atoms.

(Mercaptoorganyl)alkyl polyether silanes of the general formula I may be:

[(C$_4$H$_9$O—(CH$_2$—CH$_2$O)$_2$](Me)$_2$Si(CH$_2$)$_3$SH,
[(C$_4$H$_9$O—(CH$_2$—CH$_2$O)$_3$](Me)$_2$Si(CH$_2$)$_3$SH,
[(C$_4$H$_9$O—(CH$_2$—CH$_2$O)$_4$](Me)$_2$Si(CH$_2$)$_3$SH,
[(C$_4$H$_9$O—(CH$_2$—CH$_2$O)$_5$](Me)$_2$Si(CH$_2$)$_3$SH,
[(C$_4$H$_9$O—(CH$_2$—CH$_2$O)$_6$](Me)$_2$Si(CH$_2$)$_3$SH,
[(C$_5$H$_{11}$O—(CH$_2$—CH$_2$O)$_2$](Me)$_2$Si(CH$_2$)$_3$SH,
[(C$_5$H$_{11}$O—(CH$_2$—CH$_2$O)$_3$](Me)$_2$Si(CH$_2$)$_3$SH,
[(C$_5$H$_{11}$O—(CH$_2$—CH$_2$O)$_4$](Me)$_2$Si(CH$_2$)$_3$SH,
[(C$_5$H$_{11}$O—(CH$_2$—CH$_2$O)$_5$](Me)$_2$Si(CH$_2$)$_3$SH,
[(C$_5$H$_{11}$O—(CH$_2$—CH$_2$O)$_6$](Me)$_2$Si(CH$_2$)$_3$SH,
[(C$_6$H$_{13}$O—(CH$_2$—CH$_2$O)$_2$](Me)$_2$Si(CH$_2$)$_3$SH,
[(C$_6$H$_{13}$O—(CH$_2$—CH$_2$O)$_3$](Me)$_2$Si(CH$_2$)$_3$SH,
[(C$_6$H$_{13}$O—(CH$_2$—CH$_2$O)$_4$](Me)$_2$Si(CH$_2$)$_3$SH,
[(C$_6$H$_{13}$O—(CH$_2$—CH$_2$O)$_5$](Me)$_2$Si(CH$_2$)$_3$SH,
[(C$_6$H$_{13}$O—(CH$_2$—CH$_2$O)$_6$](Me)$_2$Si(CH$_2$)$_3$SH,
[(C$_7$H$_{15}$O—(CH$_2$—CH$_2$O)$_2$](Me)$_2$Si(CH$_2$)$_3$SH,
[(C$_7$H$_{15}$O—(CH$_2$—CH$_2$O)$_3$](Me)$_2$Si(CH$_2$)$_3$SH,
[(C$_7$H$_{15}$O—(CH$_2$—CH$_2$O)$_4$](Me)$_2$Si(CH$_2$)$_3$SH,
[(C$_7$H$_{15}$O—(CH$_2$—CH$_2$O)$_5$](Me)$_2$Si(CH$_2$)$_3$SH,
[(C$_7$H$_{15}$O—(CH$_2$—CH$_2$O)$_6$](Me)$_2$Si(CH$_2$)$_3$SH,
[(C$_8$H$_{17}$O—(CH$_2$—CH$_2$O)$_2$](Me)$_2$Si(CH$_2$)$_3$SH,
[(C$_8$H$_{17}$O—(CH$_2$—CH$_2$O)$_3$](Me)$_2$Si(CH$_2$)$_3$SH,
[(C$_8$H$_{17}$O—(CH$_2$—CH$_2$O)$_4$](Me)$_2$Si(CH$_2$)$_3$SH,
[(C$_8$H$_{17}$O—(CH$_2$—CH$_2$O)$_5$](Me)$_2$Si(CH$_2$)$_3$SH,
[(C$_8$H$_{17}$O—(CH$_2$—CH$_2$O)$_6$](Me)$_2$Si(CH$_2$)$_3$SH,
[(C$_9$H$_{19}$O—(CH$_2$—CH$_2$O)$_2$](Me)$_2$Si(CH$_2$)$_3$SH,
[(C$_9$H$_{19}$O—(CH$_2$—CH$_2$O)$_3$](Me)$_2$Si(CH$_2$)$_3$SH,
[(C$_9$H$_{19}$O—(CH$_2$—CH$_2$O)$_4$](Me)$_2$Si(CH$_2$)$_3$SH,
[(C$_9$H$_{19}$O—(CH$_2$—CH$_2$O)$_5$](Me)$_2$Si(CH$_2$)$_3$SH,
[(C$_9$H$_{19}$O—(CH$_2$—CH$_2$O)$_6$](Me)$_2$Si(CH$_2$)$_3$SH,
[(C$_4$H$_9$O—(CH$_2$—CH$_2$O)$_2$]$_2$(Me)Si(CH$_2$)$_3$SH,
[(C$_4$H$_9$O—(CH$_2$—CH$_2$O)$_3$]$_2$(Me)Si(CH$_2$)$_3$SH,
[(C$_4$H$_9$O—(CH$_2$—CH$_2$O)$_4$]$_2$(Me)Si(CH$_2$)$_3$SH,
[(C$_4$H$_9$O—(CH$_2$—CH$_2$O)$_5$]$_2$(Me)Si(CH$_2$)$_3$SH,
[(C$_4$H$_9$O—(CH$_2$—CH$_2$O)$_6$]$_2$(Me)Si(CH$_2$)$_3$SH,
[(C$_5$H$_{11}$O—(CH$_2$—CH$_2$O)$_2$]$_2$(Me)Si(CH$_2$)$_3$SH,
[(C$_5$H$_{11}$O—(CH$_2$—CH$_2$O)$_3$]$_2$(Me)Si(CH$_2$)$_3$SH,
[(C$_5$H$_{11}$O—(CH$_2$—CH$_2$O)$_4$]$_2$(Me)Si(CH$_2$)$_3$SH,
[(C$_5$H$_{11}$O—(CH$_2$—CH$_2$O)$_5$]$_2$(Me)Si(CH$_2$)$_3$SH,
[(C$_5$H$_{11}$O—(CH$_2$—CH$_2$O)$_6$]$_2$(Me)Si(CH$_2$)$_3$SH,
[(C$_6$H$_{13}$O—(CH$_2$—CH$_2$O)$_2$]$_2$(Me)Si(CH$_2$)$_3$SH,
[(C$_6$H$_{13}$O—(CH$_2$—CH$_2$O)$_3$]$_2$(Me)Si(CH$_2$)$_3$SH,
[(C$_6$H$_{13}$O—(CH$_2$—CH$_2$O)$_4$]$_2$(Me)Si(CH$_2$)$_3$SH,
[(C$_6$H$_{13}$O—(CH$_2$—CH$_2$O)$_5$]$_2$(Me)Si(CH$_2$)$_3$SH,
[(C$_6$H$_{13}$O—(CH$_2$—CH$_2$O)$_6$]$_2$(Me)Si(CH$_2$)$_3$SH,
[(C$_7$H$_{15}$O—(CH$_2$—CH$_2$O)$_2$]$_2$(Me)Si(CH$_2$)$_3$SH,
[(C$_7$H$_{15}$O—(CH$_2$—CH$_2$O)$_3$]$_2$(Me)Si(CH$_2$)$_3$SH,

[(C₇H₁₅O—(CH₂—CH₂O)₄]₂(Me)Si(CH₂)₃SH,
[(C₇H₁₅O—(CH₂—CH₂O)₅]₂(Me)Si(CH₂)₃SH,
[(C₇H₁₅O—(CH₂—CH₂O)₆]₂(Me)Si(CH₂)₃SH,
[(C₈H₁₇O—(CH₂—CH₂O)₂]₂(Me)Si(CH₂)₃SH,
[(C₈H₁₇O—(CH₂—CH₂O)₃]₂(Me)Si(CH₂)₃SH,
[(C₈H₁₇O—(CH₂—CH₂O)₄]₂(Me)Si(CH₂)₃SH,
[(C₈H₁₇O—(CH₂—CH₂O)₅]₂(Me)Si(CH₂)₃SH,
[(C₈H₁₇O—(CH₂—CH₂O)₆]₂(Me)Si(CH₂)₃SH,
[(C₉H₁₉O—(CH₂—CH₂O)₂]₂(Me)Si(CH₂)₃SH,
[(C₉H₁₉O—(CH₂—CH₂O)₃]₂(Me)Si(CH₂)₃SH,
[(C₉H₁₉O—(CH₂—CH₂O)₄]₂(Me)Si(CH₂)₃SH,
[(C₉H₁₉O—(CH₂—CH₂O)₅]₂(Me)Si(CH₂)₃SH,
[(C₉H₁₉O—(CH₂—CH₂O)₆]₂(Me)Si(CH₂)₃SH,
[(C₄H₉O—(CH₂—CH₂O)₂](Me)(EtO)Si(CH₂)₃SH,
[(C₄H₉O—(CH₂—CH₂O)₃](Me)(EtO)Si(CH₂)₃SH,
[(C₄H₉O—(CH₂—CH₂O)₄](Me)(EtO)Si(CH₂)₃SH,
[(C₄H₉O—(CH₂—CH₂O)₅](Me)(EtO)Si(CH₂)₃SH,
[(C₄H₉O—(CH₂—CH₂O)₆](Me)(EtO)Si(CH₂)₃SH,
[(C₅H₁₁O—(CH₂—CH₂O)₂](Me)(EtO)Si(CH₂)₃SH,
[(C₅H₁₁O—(CH₂—CH₂O)₃](Me)(EtO)Si(CH₂)₃SH,
[(C₅H₁₁O—(CH₂—CH₂O)₄](Me)(EtO)Si(CH₂)₃SH,
[(C₅H₁₁O—(CH₂—CH₂O)₅](Me)(EtO)Si(CH₂)₃SH,
[(C₅H₁₁O—(CH₂—CH₂O)₆](Me)(EtO)Si(CH₂)₃SH,
[(C₆H₁₃O—(CH₂—CH₂O)₂](Me)(EtO)Si(CH₂)₃SH,
[(C₆H₁₃O—(CH₂—CH₂O)₃](Me)(EtO)Si(CH₂)₃SH,
[(C₆H₁₃O—(CH₂—CH₂O)₄](Me)(EtO)Si(CH₂)₃SH,
[(C₆H₁₃O—(CH₂—CH₂O)₅](Me)(EtO)Si(CH₂)₃SH,
[(C₆H₁₃O—(CH₂—CH₂O)₆](Me)(EtO)Si(CH₂)₃SH,
[(C₇H₁₅O—(CH₂—CH₂O)₂](Me)(EtO)Si(CH₂)₃SH,
[(C₇H₁₅O—(CH₂—CH₂O)₃](Me)(EtO)Si(CH₂)₃SH,
[(C₇H₁₅O—(CH₂—CH₂O)₄](Me)(EtO)Si(CH₂)₃SH,
[(C₇H₁₅O—(CH₂—CH₂O)₅](Me)(EtO)Si(CH₂)₃SH,
[(C₇H₁₅O—(CH₂—CH₂O)₆](Me)(EtO)Si(CH₂)₃SH,
[(C₈H₁₇O—(CH₂—CH₂O)₂](Me)(EtO)Si(CH₂)₃SH,
[(C₈H₁₇O—(CH₂—CH₂O)₃](Me)(EtO)Si(CH₂)₃SH,
[(C₈H₁₇O—(CH₂—CH₂O)₄](Me)(EtO)Si(CH₂)₃SH,
[(C₈H₁₇O—(CH₂—CH₂O)₅](Me)(EtO)Si(CH₂)₃SH,
[(C₈H₁₇O—(CH₂—CH₂O)₆](Me)(EtO)Si(CH₂)₃SH,
[(C₉H₁₉O—(CH₂—CH₂O)₂](Me)(EtO)Si(CH₂)₃SH,
[(C₉H₁₉O—(CH₂—CH₂O)₃](Me)(EtO)Si(CH₂)₃SH,
[(C₉H₁₉O—(CH₂—CH₂O)₄](Me)(EtO)Si(CH₂)₃SH,
[(C₉H₁₉O—(CH₂—CH₂O)₅](Me)(EtO)Si(CH₂)₃SH,
[(C₉H₁₉O—(CH₂—CH₂O)₆](Me)(EtO)Si(CH₂)₃SH,
[(C₁₀H₂₁O—(CH₂—CH₂O)₂](Me)(EtO)Si(CH₂)₃SH,
[(C₁₀H₂₁O—(CH₂—CH₂O)₃](Me)(EtO)Si(CH₂)₃SH,
[(C₁₀H₂₁O—(CH₂—CH₂O)₄](Me)(EtO)Si(CH₂)₃SH,
[(C₁₀H₂₁O—(CH₂—CH₂O)₅](Me)(EtO)Si(CH₂)₃SH,
[(C₁₀H₂₁O—(CH₂—CH₂O)₆](Me)(EtO)Si(CH₂)₃SH,
[(C₁₁H₂₃O—(CH₂—CH₂O)₂](Me)(EtO)Si(CH₂)₃SH,
[(C₁₁H₂₃O—(CH₂—CH₂O)₃](Me)(EtO)Si(CH₂)₃SH,
[(C₁₁H₂₃O—(CH₂—CH₂O)₄](Me)(EtO)Si(CH₂)₃SH,
[(C₁₁H₂₃O—(CH₂—CH₂O)₅](Me)(EtO)Si(CH₂)₃SH,
[(C₁₁H₂₃O—(CH₂—CH₂O)₆](Me)(EtO)Si(CH₂)₃SH,
[(C₁₂H₂₅O—(CH₂—CH₂O)₂](Me)(EtO)Si(CH₂)₃SH,
[(C₁₂H₂₅O—(CH₂—CH₂O)₃](Me)(EtO)Si(CH₂)₃SH,
[(C₁₂H₂₅O—(CH₂—CH₂O)₄](Me)(EtO)Si(CH₂)₃SH,
[(C₁₂H₂₅O—(CH₂—CH₂O)₅](Me)(EtO)Si(CH₂)₃SH,
[(C₁₂H₂₅O—(CH₂—CH₂O)₆](Me)(EtO)Si(CH₂)₃SH,
[(C₁₃H₂₇O—(CH₂—CH₂O)₂](Me)(EtO)Si(CH₂)₃SH,
[(C₁₃H₂₇O—(CH₂—CH₂O)₃](Me)(EtO)Si(CH₂)₃SH,
[(C₁₃H₂₇O—(CH₂—CH₂O)₄](Me)(EtO)Si(CH₂)₃SH,
[(C₁₃H₂₇O—(CH₂—CH₂O)₅](Me)(EtO)Si(CH₂)₃SH,
[(C₁₃H₂₇O—(CH₂—CH₂O)₆](Me)(EtO)Si(CH₂)₃SH,
[(C₁₄H₂₉O—(CH₂—CH₂O)₂](Me)(EtO)Si(CH₂)₃SH,
[(C₁₄H₂₉O—(CH₂—CH₂O)₃](Me)(EtO)Si(CH₂)₃SH,
[(C₁₄H₂₉O—(CH₂—CH₂O)₄](Me)(EtO)Si(CH₂)₃SH,
[(C₁₄H₂₉O—(CH₂—CH₂O)₅](Me)(EtO)Si(CH₂)₃SH,

[(C₁₄H₂₉O—(CH₂—CH₂O)₆](Me)(EtO)Si(CH₂)₃SH,
[(C₁₅H₃₁O—(CH₂—CH₂O)₂](Me)(EtO)Si(CH₂)₃SH,
[(C₁₅H₃₁O—(CH₂—CH₂O)₃](Me)(EtO)Si(CH₂)₃SH,
[(C₁₅H₃₁O—(CH₂—CH₂O)₄](Me)(EtO)Si(CH₂)₃SH,
[(C₁₅H₃₁O—(CH₂—CH₂O)₅](Me)(EtO)Si(CH₂)₃SH,
[(C₁₅H₃₁O—(CH₂—CH₂O)₆](Me)(EtO)Si(CH₂)₃SH,
[(C₁₆H₃₃O—(CH₂—CH₂O)₂](Me)(EtO)Si(CH₂)₃SH,
[(C₁₆H₃₃O—(CH₂—CH₂O)₃](Me)(EtO)Si(CH₂)₃SH,
[(C₁₆H₃₃O—(CH₂—CH₂O)₄](Me)(EtO)Si(CH₂)₃SH,
[(C₁₆H₃₃O—(CH₂—CH₂O)₅](Me)(EtO)Si(CH₂)₃SH,
[(C₁₆H₃₃O—(CH₂—CH₂O)₆](Me)(EtO)Si(CH₂)₃SH,
[(C₁₇H₃₅O—(CH₂—CH₂O)₂](Me)(EtO)Si(CH₂)₃SH,
[(C₁₇H₃₅O—(CH₂—CH₂O)₃](Me)(EtO)Si(CH₂)₃SH,
[(C₁₇H₃₅O—(CH₂—CH₂O)₄](Me)(EtO)Si(CH₂)₃SH,
[(C₁₇H₃₅O—(CH₂—CH₂O)₅](Me)(EtO)Si(CH₂)₃SH,
[(C₁₇H₃₅O—(CH₂—CH₂O)₆](Me)(EtO)Si(CH₂)₃SH,
[(C₁₈H₃₇O—(CH₂—CH₂O)₂](Me)(EtO)Si(CH₂)₃SH,
[(C₁₈H₃₇O—(CH₂—CH₂O)₃](Me)(EtO)Si(CH₂)₃SH,
[(C₁₈H₃₇O—(CH₂—CH₂O)₄](Me)(EtO)Si(CH₂)₃SH,
[(C₁₈H₃₇O—(CH₂—CH₂O)₅](Me)(EtO)Si(CH₂)₃SH,
[(C₁₈H₃₇O—(CH₂—CH₂O)₆](Me)(EtO)Si(CH₂)₃SH,
[(C₄H₉O—(CH₂—CH₂O)₂](Me)(MeO)Si(CH₂)₃SH,
[(C₄H₉O—(CH₂—CH₂O)₃](Me)(MeO)Si(CH₂)₃SH,
[(C₄H₉O—(CH₂—CH₂O)₄](Me)(MeO)Si(CH₂)₃SH,
[(C₄H₉O—(CH₂—CH₂O)₅](Me)(MeO)Si(CH₂)₃SH,
[(C₄H₉O—(CH₂—CH₂O)₆](Me)(MeO)Si(CH₂)₃SH,
[(C₅H₁₁O—(CH₂—CH₂O)₂](Me)(MeO)Si(CH₂)₃SH,
[(C₅H₁₁O—(CH₂—CH₂O)₃](Me)(MeO)Si(CH₂)₃SH,
[(C₅H₁₁O—(CH₂—CH₂O)₄](Me)(MeO)Si(CH₂)₃SH,
[(C₅H₁₁O—(CH₂—CH₂O)₅](Me)(MeO)Si(CH₂)₃SH,
[(C₅H₁₁O—(CH₂—CH₂O)₆](Me)(MeO)Si(CH₂)₃SH,
[(C₆H₁₃O—(CH₂—CH₂O)₂](Me)(MeO)Si(CH₂)₃SH,
[(C₆H₁₃O—(CH₂—CH₂O)₃](Me)(MeO)Si(CH₂)₃SH,
[(C₆H₁₃O—(CH₂—CH₂O)₄](Me)(MeO)Si(CH₂)₃SH,
[(C₆H₁₃O—(CH₂—CH₂O)₅](Me)(MeO)Si(CH₂)₃SH,
[(C₆H₁₃O—(CH₂—CH₂O)₆](Me)(MeO)Si(CH₂)₃SH,
[(C₇H₁₅O—(CH₂—CH₂O)₂](Me)(MeO)Si(CH₂)₃SH,
[(C₇H₁₅O—(CH₂—CH₂O)₃](Me)(MeO)Si(CH₂)₃SH,
[(C₇H₁₅O—(CH₂—CH₂O)₄](Me)(MeO)Si(CH₂)₃SH,
[(C₇H₁₅O—(CH₂—CH₂O)₅](Me)(MeO)Si(CH₂)₃SH,
[(C₇H₁₅O—(CH₂—CH₂O)₆](Me)(MeO)Si(CH₂)₃SH,
[(C₈H₁₇O—(CH₂—CH₂O)₂](Me)(MeO)Si(CH₂)₃SH,
[(C₈H₁₇O—(CH₂—CH₂O)₃](Me)(MeO)Si(CH₂)₃SH,
[(C₈H₁₇O—(CH₂—CH₂O)₄](Me)(MeO)Si(CH₂)₃SH,
[(C₈H₁₇O—(CH₂—CH₂O)₅](Me)(MeO)Si(CH₂)₃SH,
[(C₈H₁₇O—(CH₂—CH₂O)₆](Me)(MeO)Si(CH₂)₃SH,
[(C₉H₁₉O—(CH₂—CH₂O)₂](Me)(MeO)Si(CH₂)₃SH,
[(C₉H₁₉O—(CH₂—CH₂O)₃](Me)(MeO)Si(CH₂)₃SH,
[(C₉H₁₉O—(CH₂—CH₂O)₄](Me)(MeO)Si(CH₂)₃SH,
[(C₉H₁₉O—(CH₂—CH₂O)₅](Me)(MeO)Si(CH₂)₃SH,
[(C₉H₁₉O—(CH₂—CH₂O)₆](Me)(MeO)Si(CH₂)₃SH,
[(C₄H₉O—(CH₂—CH₂O)₂](MeO)₂Si(CH₂)₃SH,
[(C₄H₉O—(CH₂—CH₂O)₃](MeO)₂Si(CH₂)₃SH,
[(C₄H₉O—(CH₂—CH₂O)₄](MeO)₂Si(CH₂)₃SH,
[(C₄H₉O—(CH₂—CH₂O)₅](MeO)₂Si(CH₂)₃SH,
[(C₄H₉O—(CH₂—CH₂O)₆](MeO)₂Si(CH₂)₃SH,
[(C₅H₁₁O—(CH₂—CH₂O)₂](MeO)₂Si(CH₂)₃SH,
[(C₅H₁₁O—(CH₂—CH₂O)₃](MeO)₂Si(CH₂)₃SH,
[(C₅H₁₁O—(CH₂—CH₂O)₄](MeO)₂Si(CH₂)₃SH,
[(C₅H₁₁O—(CH₂—CH₂O)₅](MeO)₂Si(CH₂)₃SH,
[(C₅H₁₁O—(CH₂—CH₂O)₆](MeO)₂Si(CH₂)₃SH,
[(C₆H₁₃O—(CH₂—CH₂O)₂](MeO)₂Si(CH₂)₃SH,
[(C₆H₁₃O—(CH₂—CH₂O)₃](MeO)₂Si(CH₂)₃SH,
[(C₆H₁₃O—(CH₂—CH₂O)₄](MeO)₂Si(CH₂)₃SH,
[(C₆H₁₃O—(CH₂—CH₂O)₅](MeO)₂Si(CH₂)₃SH,
[(C₆H₁₃O—(CH₂—CH₂O)₆](MeO)₂Si(CH₂)₃SH,
[(C₇H₁₅O—(CH₂—CH₂O)₂](MeO)₂Si(CH₂)₃SH,

[(C$_7$H$_{15}$O—(CH$_2$—CH$_2$O)$_3$](MeO)$_2$Si(CH$_2$)$_3$SH,
[(C$_7$H$_{15}$O—(CH$_2$—CH$_2$O)$_4$](MeO)$_2$Si(CH$_2$)$_3$SH,
[(C$_7$H$_{15}$O—(CH$_2$—CH$_2$O)$_5$](MeO)$_2$Si(CH$_2$)$_3$SH,
[(C$_7$H$_{15}$O—(CH$_2$—CH$_2$O)$_6$](MeO)$_2$Si(CH$_2$)$_3$SH,
[(C$_8$H$_{17}$O—(CH$_2$—CH$_2$O)$_2$](MeO)$_2$Si(CH$_2$)$_3$SH,
[(C$_8$H$_{17}$O—(CH$_2$—CH$_2$O)$_3$](MeO)$_2$Si(CH$_2$)$_3$SH,
[(C$_8$H$_{17}$O—(CH$_2$—CH$_2$O)$_4$](MeO)$_2$Si(CH$_2$)$_3$SH,
[(C$_8$H$_{17}$O—(CH$_2$—CH$_2$O)$_5$](MeO)$_2$Si(CH$_2$)$_3$SH,
[(C$_8$H$_{17}$O—(CH$_2$—CH$_2$O)$_6$](MeO)$_2$Si(CH$_2$)$_3$SH,
[(C$_9$H$_{19}$O—(CH$_2$—CH$_2$O)$_2$](MeO)$_2$Si(CH$_2$)$_3$SH,
[(C$_9$H$_{19}$O—(CH$_2$—CH$_2$O)$_3$](MeO)$_2$Si(CH$_2$)$_3$SH,
[(C$_9$H$_{19}$O—(CH$_2$—CH$_2$O)$_4$](MeO)$_2$Si(CH$_2$)$_3$SH,
[(C$_9$H$_{19}$O—(CH$_2$—CH$_2$O)$_5$](MeO)$_2$Si(CH$_2$)$_3$SH,
[(C$_9$H$_{19}$O—(CH$_2$—CH$_2$O)$_6$](MeO)$_2$Si(CH$_2$)$_3$SH,
[(C$_{10}$H$_{21}$O—(CH$_2$—CH$_2$O)$_2$](MeO)$_2$Si(CH$_2$)$_3$SH,
[(C$_{10}$H$_{21}$O—(CH$_2$—CH$_2$O)$_3$](MeO)$_2$Si(CH$_2$)$_3$SH,
[(C$_{10}$H$_{21}$O—(CH$_2$—CH$_2$O)$_4$](MeO)$_2$Si(CH$_2$)$_3$SH,
[(C$_{10}$H$_{21}$O—(CH$_2$—CH$_2$O)$_5$](MeO)$_2$Si(CH$_2$)$_3$SH,
[(C$_{10}$H$_{21}$O—(CH$_2$—CH$_2$O)$_6$](MeO)$_2$Si(CH$_2$)$_3$SH,
[(C$_{11}$H$_{23}$O—(CH$_2$—CH$_2$O)$_2$](MeO)$_2$Si(CH$_2$)$_3$SH,
[(C$_{11}$H$_{23}$O—(CH$_2$—CH$_2$O)$_3$](MeO)$_2$Si(CH$_2$)$_3$SH,
[(C$_{11}$H$_{23}$O—(CH$_2$—CH$_2$O)$_4$](MeO)$_2$Si(CH$_2$)$_3$SH,
[(C$_{11}$H$_{23}$O—(CH$_2$—CH$_2$O)$_5$](MeO)$_2$Si(CH$_2$)$_3$SH,
[(C$_{11}$H$_{23}$O—(CH$_2$—CH$_2$O)$_6$](MeO)$_2$Si(CH$_2$)$_3$SH,
[(C$_{12}$H$_{25}$O—(CH$_2$—CH$_2$O)$_2$](MeO)$_2$Si(CH$_2$)$_3$SH,
[(C$_{12}$H$_{25}$O—(CH$_2$—CH$_2$O)$_3$](MeO)$_2$Si(CH$_2$)$_3$SH,
[(C$_{12}$H$_{25}$O—(CH$_2$—CH$_2$O)$_4$](MeO)$_2$Si(CH$_2$)$_3$SH,
[(C$_{12}$H$_{25}$O—(CH$_2$—CH$_2$O)$_5$](MeO)$_2$Si(CH$_2$)$_3$SH,
[(C$_{12}$H$_{25}$O—(CH$_2$—CH$_2$O)$_6$](MeO)$_2$Si(CH$_2$)$_3$SH,
[(C$_{13}$H$_{27}$O—(CH$_2$—CH$_2$O)$_2$](MeO)$_2$Si(CH$_2$)$_3$SH,
[(C$_{13}$H$_{27}$O—(CH$_2$—CH$_2$O)$_3$](MeO)$_2$Si(CH$_2$)$_3$SH,
[(C$_{13}$H$_{27}$O—(CH$_2$—CH$_2$O)$_4$](MeO)$_2$Si(CH$_2$)$_3$SH,
[(C$_{13}$H$_{27}$O—(CH$_2$—CH$_2$O)$_5$](MeO)$_2$Si(CH$_2$)$_3$SH,
[(C$_{13}$H$_{27}$O—(CH$_2$—CH$_2$O)$_6$](MeO)$_2$Si(CH$_2$)$_3$SH,
[(C$_{14}$H$_{29}$O—(CH$_2$—CH$_2$O)$_2$](MeO)$_2$Si(CH$_2$)$_3$SH,
[(C$_{14}$H$_{29}$O—(CH$_2$—CH$_2$O)$_3$](MeO)$_2$Si(CH$_2$)$_3$SH,
[(C$_{14}$H$_{29}$O—(CH$_2$—CH$_2$O)$_4$](MeO)$_2$Si(CH$_2$)$_3$SH,
[(C$_{14}$H$_{29}$O—(CH$_2$—CH$_2$O)$_5$](MeO)$_2$Si(CH$_2$)$_3$SH,
[(C$_{14}$H$_{29}$O—(CH$_2$—CH$_2$O)$_6$](MeO)$_2$Si(CH$_2$)$_3$SH,
[(C$_{16}$H$_{33}$O—(CH$_2$—CH$_2$O)$_2$](MeO)$_2$Si(CH$_2$)$_3$SH,
[(C$_{16}$H$_{33}$O—(CH$_2$—CH$_2$O)$_3$](MeO)$_2$Si(CH$_2$)$_3$SH,
[(C$_{16}$H$_{33}$O—(CH$_2$—CH$_2$O)$_4$](MeO)$_2$Si(CH$_2$)$_3$SH,
[(C$_{16}$H$_{33}$O—(CH$_2$—CH$_2$O)$_5$](MeO)$_2$Si(CH$_2$)$_3$SH,
[(C$_{16}$H$_{33}$O—(CH$_2$—CH$_2$O)$_6$](MeO)$_2$Si(CH$_2$)$_3$SH,
[(C$_{18}$H$_{37}$O—(CH$_2$—CH$_2$O)$_2$](MeO)$_2$Si(CH$_2$)$_3$SH,
[(C$_{18}$H$_{37}$O—(CH$_2$—CH$_2$O)$_3$](MeO)$_2$Si(CH$_2$)$_3$SH,
[(C$_{18}$H$_{37}$O—(CH$_2$—CH$_2$O)$_4$](MeO)$_2$Si(CH$_2$)$_3$SH,
[(C$_{18}$H$_{37}$O—(CH$_2$—CH$_2$O)$_5$](MeO)$_2$Si(CH$_2$)$_3$SH,
[(C$_{18}$H$_{37}$O—(CH$_2$—CH$_2$O)$_6$](MeO)$_2$Si(CH$_2$)$_3$SH,
[(C$_9$H$_{19}$O—(CH$_2$—CH$_2$O)$_2$]$_2$(MeO)Si(CH$_2$)$_3$SH,
[(C$_9$H$_{19}$O—(CH$_2$—CH$_2$O)$_3$]$_2$(MeO)Si(CH$_2$)$_3$SH,
[(C$_9$H$_{19}$O—(CH$_2$—CH$_2$O)$_4$]$_2$(MeO)Si(CH$_2$)$_3$SH,
[(C$_9$H$_{19}$O—(CH$_2$—CH$_2$O)$_5$]$_2$(MeO)Si(CH$_2$)$_3$SH,
[(C$_9$H$_{19}$O—(CH$_2$—CH$_2$O)$_6$]$_2$(MeO)Si(CH$_2$)$_3$SH,
[(C$_{12}$H$_{25}$O—(CH$_2$—CH$_2$O)$_2$]$_2$(MeO)Si(CH$_2$)$_3$SH,
[(C$_{12}$H$_{25}$O—(CH$_2$—CH$_2$O)$_3$]$_2$(MeO)Si(CH$_2$)$_3$SH,
[(C$_{12}$H$_{25}$O—(CH$_2$—CH$_2$O)$_4$]$_2$(MeO)Si(CH$_2$)$_3$SH,
[(C$_{12}$H$_{25}$O—(CH$_2$—CH$_2$O)$_5$]$_2$(MeO)Si(CH$_2$)$_3$SH,
[(C$_{12}$H$_{25}$O—(CH$_2$—CH$_2$O)$_6$]$_2$(MeO)Si(CH$_2$)$_3$SH,
[(C$_{13}$H$_{27}$O—(CH$_2$—CH$_2$O)$_2$]$_2$(MeO)Si(CH$_2$)$_3$SH,
[(C$_{13}$H$_{27}$O—(CH$_2$—CH$_2$O)$_3$]$_2$(MeO)Si(CH$_2$)$_3$SH,
[(C$_{13}$H$_{27}$O—(CH$_2$—CH$_2$O)$_4$]$_2$(MeO)Si(CH$_2$)$_3$SH,
[(C$_{13}$H$_{27}$O—(CH$_2$—CH$_2$O)$_5$]$_2$(MeO)Si(CH$_2$)$_3$SH,
[(C$_{13}$H$_{27}$O—(CH$_2$—CH$_2$O)$_6$]$_2$(MeO)Si(CH$_2$)$_3$SH,
[(C$_{14}$H$_{29}$O—(CH$_2$—CH$_2$O)$_2$]$_2$(MeO)Si(CH$_2$)$_3$SH,
[(C$_{14}$H$_{29}$O—(CH$_2$—CH$_2$O)$_3$]$_2$(MeO)Si(CH$_2$)$_3$SH,
[(C$_{14}$H$_{29}$O—(CH$_2$—CH$_2$O)$_4$]$_2$(MeO)Si(CH$_2$)$_3$SH,
[(C$_{14}$H$_{29}$O—(CH$_2$—CH$_2$O)$_5$]$_2$(MeO)Si(CH$_2$)$_3$SH,
[(C$_{14}$H$_{29}$O—(CH$_2$—CH$_2$O)$_6$]$_2$(MeO)Si(CH$_2$)$_3$SH,
[(C$_{16}$H$_{33}$O—(CH$_2$—CH$_2$O)$_2$]$_2$(MeO)Si(CH$_2$)$_3$SH,
[(C$_{16}$H$_{33}$O—(CH$_2$—CH$_2$O)$_3$]$_2$(MeO)Si(CH$_2$)$_3$SH,
[(C$_{16}$H$_{33}$O—(CH$_2$—CH$_2$O)$_4$]$_2$(MeO)Si(CH$_2$)$_3$SH,
[(C$_{16}$H$_{33}$O—(CH$_2$—CH$_2$O)$_5$]$_2$(MeO)Si(CH$_2$)$_3$SH,
[(C$_{16}$H$_{33}$O—(CH$_2$—CH$_2$O)$_6$]$_2$(MeO)Si(CH$_2$)$_3$SH,
[(C$_{18}$H$_{37}$O—(CH$_2$—CH$_2$O)$_2$]$_2$(MeO)Si(CH$_2$)$_3$SH,
[(C$_{18}$H$_{37}$O—(CH$_2$—CH$_2$O)$_3$]$_2$(MeO)Si(CH$_2$)$_3$SH,
[(C$_{18}$H$_{37}$O—(CH$_2$—CH$_2$O)$_4$]$_2$(MeO)Si(CH$_2$)$_3$SH,
[(C$_{18}$H$_{37}$O—(CH$_2$—CH$_2$O)$_5$]$_2$(MeO)Si(CH$_2$)$_3$SH,
[(C$_{18}$H$_{37}$O—(CH$_2$—CH$_2$O)$_6$]$_2$(MeO)Si(CH$_2$)$_3$SH,
[(C$_4$H$_9$O—(CH$_2$—CH$_2$O)$_2$](EtO)$_2$Si(CH$_2$)$_3$SH,
[(C$_4$H$_9$O—(CH$_2$—CH$_2$O)$_3$](EtO)$_2$Si(CH$_2$)$_3$SH,
[(C$_4$H$_9$O—(CH$_2$—CH$_2$O)$_4$](EtO)$_2$Si(CH$_2$)$_3$SH,
[(C$_4$H$_9$O—(CH$_2$—CH$_2$O)$_5$](EtO)$_2$Si(CH$_2$)$_3$SH,
[(C$_4$H$_9$O—(CH$_2$—CH$_2$O)$_6$](EtO)$_2$Si(CH$_2$)$_3$SH,
[(C$_5$H$_{11}$O—(CH$_2$—CH$_2$O)$_2$](EtO)$_2$Si(CH$_2$)$_3$SH,
[(C$_5$H$_{11}$O—(CH$_2$—CH$_2$O)$_3$](EtO)$_2$Si(CH$_2$)$_3$SH,
[(C$_5$H$_{11}$O—(CH$_2$—CH$_2$O)$_4$](EtO)$_2$Si(CH$_2$)$_3$SH,
[(C$_5$H$_{11}$O—(CH$_2$—CH$_2$O)$_5$](EtO)$_2$Si(CH$_2$)$_3$SH,
[(C$_5$H$_{11}$O—(CH$_2$—CH$_2$O)$_6$](EtO)$_2$Si(CH$_2$)$_3$SH,
[(C$_6$H$_{13}$O—(CH$_2$—CH$_2$O)$_2$](EtO)$_2$Si(CH$_2$)$_3$SH,
[(C$_6$H$_{13}$O—(CH$_2$—CH$_2$O)$_3$](EtO)$_2$Si(CH$_2$)$_3$SH,
[(C$_6$H$_{13}$O—(CH$_2$—CH$_2$O)$_4$](EtO)$_2$Si(CH$_2$)$_3$SH,
[(C$_6$H$_{13}$O—(CH$_2$—CH$_2$O)$_5$](EtO)$_2$Si(CH$_2$)$_3$SH,
[(C$_6$H$_{13}$O—(CH$_2$—CH$_2$O)$_6$](EtO)$_2$Si(CH$_2$)$_3$SH,
[(C$_7$H$_{15}$O—(CH$_2$—CH$_2$O)$_2$](EtO)$_2$Si(CH$_2$)$_3$SH,
[(C$_7$H$_{15}$O—(CH$_2$—CH$_2$O)$_3$](EtO)$_2$Si(CH$_2$)$_3$SH,
[(C$_7$H$_{15}$O—(CH$_2$—CH$_2$O)$_4$](EtO)$_2$Si(CH$_2$)$_3$SH,
[(C$_7$H$_{15}$O—(CH$_2$—CH$_2$O)$_5$](EtO)$_2$Si(CH$_2$)$_3$SH,
[(C$_7$H$_{15}$O—(CH$_2$—CH$_2$O)$_6$](EtO)$_2$Si(CH$_2$)$_3$SH,
[(C$_8$H$_{17}$O—(CH$_2$—CH$_2$O)$_2$](EtO)$_2$Si(CH$_2$)$_3$SH,
[(C$_8$H$_{17}$O—(CH$_2$—CH$_2$O)$_3$](EtO)$_2$Si(CH$_2$)$_3$SH,
[(C$_8$H$_{17}$O—(CH$_2$—CH$_2$O)$_4$](EtO)$_2$Si(CH$_2$)$_3$SH,
[(C$_8$H$_{17}$O—(CH$_2$—CH$_2$O)$_5$](EtO)$_2$Si(CH$_2$)$_3$SH,
[(C$_8$H$_{17}$O—(CH$_2$—CH$_2$O)$_6$](EtO)$_2$Si(CH$_2$)$_3$SH,
[(C$_9$H$_{19}$O—(CH$_2$—CH$_2$O)$_2$](EtO)$_2$Si(CH$_2$)$_3$SH,
[(C$_9$H$_{19}$O—(CH$_2$—CH$_2$O)$_3$](EtO)$_2$Si(CH$_2$)$_3$SH,
[(C$_9$H$_{19}$O—(CH$_2$—CH$_2$O)$_4$](EtO)$_2$Si(CH$_2$)$_3$SH,
[(C$_9$H$_{19}$O—(CH$_2$—CH$_2$O)$_5$](EtO)$_2$Si(CH$_2$)$_3$SH,
[(C$_9$H$_{19}$O—(CH$_2$—CH$_2$O)$_6$](EtO)$_2$Si(CH$_2$)$_3$SH,
[(C$_{10}$H$_{21}$O—(CH$_2$—CH$_2$O)$_2$](EtO)$_2$Si(CH$_2$)$_3$SH,
[(C$_{10}$H$_{21}$O—(CH$_2$—CH$_2$O)$_3$](EtO)$_2$Si(CH$_2$)$_3$SH,
[(C$_{10}$H$_{21}$O—(CH$_2$—CH$_2$O)$_4$](EtO)$_2$Si(CH$_2$)$_3$SH,
[(C$_{10}$H$_{21}$O—(CH$_2$—CH$_2$O)$_5$](EtO)$_2$Si(CH$_2$)$_3$SH,
[(C$_{10}$H$_{21}$O—(CH$_2$—CH$_2$O)$_6$](EtO)$_2$Si(CH$_2$)$_3$SH,
[(C$_{11}$H$_{23}$O—(CH$_2$—CH$_2$O)$_2$](EtO)$_2$Si(CH$_2$)$_3$SH,
[(C$_{11}$H$_{23}$O—(CH$_2$—CH$_2$O)$_3$](EtO)$_2$Si(CH$_2$)$_3$SH,
[(C$_{11}$H$_{23}$O—(CH$_2$—CH$_2$O)$_4$](EtO)$_2$Si(CH$_2$)$_3$SH,
[(C$_{11}$H$_{23}$O—(CH$_2$—CH$_2$O)$_5$](EtO)$_2$Si(CH$_2$)$_3$SH,
[(C$_{11}$H$_{23}$O—(CH$_2$—CH$_2$O)$_6$](EtO)$_2$Si(CH$_2$)$_3$SH,
[(C$_{12}$H$_{25}$O—(CH$_2$—CH$_2$O)$_2$](EtO)$_2$Si(CH$_2$)$_3$SH,
[(C$_{12}$H$_{25}$O—(CH$_2$—CH$_2$O)$_3$](EtO)$_2$Si(CH$_2$)$_3$SH,
[(C$_{12}$H$_{25}$O—(CH$_2$—CH$_2$O)$_4$](EtO)$_2$Si(CH$_2$)$_3$SH,
[(C$_{12}$H$_{25}$O—(CH$_2$—CH$_2$O)$_5$](EtO)$_2$Si(CH$_2$)$_3$SH,
[(C$_{12}$H$_{25}$O—(CH$_2$—CH$_2$O)$_6$](EtO)$_2$Si(CH$_2$)$_3$SH,
[(C$_{13}$H$_{27}$O—(CH$_2$—CH$_2$O)$_2$](EtO)$_2$Si(CH$_2$)$_3$SH,
[(C$_{13}$H$_{27}$O—(CH$_2$—CH$_2$O)$_3$](EtO)$_2$Si(CH$_2$)$_3$SH,
[(C$_{13}$H$_{27}$O—(CH$_2$—CH$_2$O)$_4$](EtO)$_2$Si(CH$_2$)$_3$SH,
[(C$_{13}$H$_{27}$O—(CH$_2$—CH$_2$O)$_5$](EtO)$_2$Si(CH$_2$)$_3$SH,
[(C$_{13}$H$_{27}$O—(CH$_2$—CH$_2$O)$_6$](EtO)$_2$Si(CH$_2$)$_3$SH,
[(C$_{14}$H$_{29}$O—(CH$_2$—CH$_2$O)$_2$](EtO)$_2$Si(CH$_2$)$_3$SH,
[(C$_{14}$H$_{29}$O—(CH$_2$—CH$_2$O)$_3$](EtO)$_2$Si(CH$_2$)$_3$SH,
[(C$_{14}$H$_{29}$O—(CH$_2$—CH$_2$O)$_4$](EtO)$_2$Si(CH$_2$)$_3$SH,
[(C$_{14}$H$_{29}$O—(CH$_2$—CH$_2$O)$_5$](EtO)$_2$Si(CH$_2$)$_3$SH,
[(C$_{14}$H$_{29}$O—(CH$_2$—CH$_2$O)$_6$](EtO)$_2$Si(CH$_2$)$_3$SH,

[(C₁₆H₃₃O—(CH₂—CH₂O)₂](EtO)₂Si(CH₂)₃SH,
[(C₁₆H₃₃O—(CH₂—CH₂O)₃](EtO)₂Si(CH₂)₃SH,
[(C₁₆H₃₃O—(CH₂—CH₂O)₄](EtO)₂Si(CH₂)₃SH,
[(C₁₆H₃₃O—(CH₂—CH₂O)₅](EtO)₂Si(CH₂)₃SH,
[(C₁₆H₃₃O—(CH₂—CH₂O)₆](EtO)₂Si(CH₂)₃SH,
[(C₁₇H₃₅O—(CH₂—CH₂O)₂](EtO)₂Si(CH₂)₃SH,
[(C₁₇H₃₅O—(CH₂—CH₂O)₃](EtO)₂Si(CH₂)₃SH,
[(C₁₇H₃₅O—(CH₂—CH₂O)₄](EtO)₂Si(CH₂)₃SH,
[(C₁₇H₃₅O—(CH₂—CH₂O)₅](EtO)₂Si(CH₂)₃SH,
[(C₁₇H₃₅O—(CH₂—CH₂O)₆](EtO)₂Si(CH₂)₃SH,
[(C₁₈H₃₇O—(CH₂—CH₂O)₂](EtO)₂Si(CH₂)₃SH,
[(C₁₈H₃₇O—(CH₂—CH₂O)₃](EtO)₂Si(CH₂)₃SH,
[(C₁₈H₃₇O—(CH₂—CH₂O)₄](EtO)₂Si(CH₂)₃SH,
[(C₁₈H₃₇O—(CH₂—CH₂O)₅](EtO)₂Si(CH₂)₃SH,
[(C₁₈H₃₇O—(CH₂—CH₂O)₆](EtO)₂Si(CH₂)₃SH,
[(C₉H₁₉O—(CH₂—CH₂O)₂]₂(EtO)Si(CH₂)₃SH,
[(C₉H₁₉O—(CH₂—CH₂O)₃]₂(EtO)Si(CH₂)₃SH,
[(C₉H₁₉O—(CH₂—CH₂O)₄]₂(EtO)Si(CH₂)₃SH,
[(C₉H₁₉O—(CH₂—CH₂O)₅]₂(EtO)Si(CH₂)₃SH,
[(C₉H₁₉O—(CH₂—CH₂O)₆]₂(EtO)Si(CH₂)₃SH,
[(C₁₂H₂₅O—(CH₂—CH₂O)₂]₂(EtO)Si(CH₂)₃SH,
[(C₁₂H₂₅O—(CH₂—CH₂O)₃]₂(EtO)Si(CH₂)₃SH,
[(C₁₂H₂₅O—(CH₂—CH₂O)₄]₂(EtO)Si(CH₂)₃SH,
[(C₁₂H₂₅O—(CH₂—CH₂O)₅]₂(EtO)Si(CH₂)₃SH,
[(C₁₂H₂₅O—(CH₂—CH₂O)₆]₂(EtO)Si(CH₂)₃SH,
[(C₁₃H₂₇O—(CH₂—CH₂O)₂]₂(EtO)Si(CH₂)₃SH,
[(C₁₃H₂₇O—(CH₂—CH₂O)₃]₂(EtO)Si(CH₂)₃SH,
[(C₁₃H₂₇O—(CH₂—CH₂O)₄]₂(EtO)Si(CH₂)₃SH,
[(C₁₃H₂₇O—(CH₂—CH₂O)₅]₂(EtO)Si(CH₂)₃SH,
[(C₁₃H₂₇O—(CH₂—CH₂O)₆]₂(EtO)Si(CH₂)₃SH,
[(C₁₄H₂₉O—(CH₂—CH₂O)₂]₂(EtO)Si(CH₂)₃SH,
[(C₁₄H₂₉O—(CH₂—CH₂O)₃]₂(EtO)Si(CH₂)₃SH,
[(C₁₄H₂₉O—(CH₂—CH₂O)₄]₂(EtO)Si(CH₂)₃SH,
[(C₁₄H₂₉O—(CH₂—CH₂O)₅]₂(EtO)Si(CH₂)₃SH,
[(C₁₄H₂₉O—(CH₂—CH₂O)₆]₂(EtO)Si(CH₂)₃SH,
[(C₁₆H₃₃O—(CH₂—CH₂O)₂]₂(EtO)Si(CH₂)₃SH,
[(C₁₆H₃₃O—(CH₂—CH₂O)₃]₂(EtO)Si(CH₂)₃SH,
[(C₁₆H₃₃O—(CH₂—CH₂O)₄]₂(EtO)Si(CH₂)₃SH,
[(C₁₆H₃₃O—(CH₂—CH₂O)₅]₂(EtO)Si(CH₂)₃SH,
[(C₁₆H₃₃O—(CH₂—CH₂O)₆]₂(EtO)Si(CH₂)₃SH,
[(C₁₇H₃₅O—(CH₂—CH₂O)₂]₂(EtO)Si(CH₂)₃SH,
[(C₁₇H₃₅O—(CH₂—CH₂O)₃]₂(EtO)Si(CH₂)₃SH,
[(C₁₇H₃₅O—(CH₂—CH₂O)₄]₂(EtO)Si(CH₂)₃SH,
[(C₁₇H₃₅O—(CH₂—CH₂O)₅]₂(EtO)Si(CH₂)₃SH,
[(C₁₇H₃₅O—(CH₂—CH₂O)₆]₂(EtO)Si(CH₂)₃SH,
[(C₁₈H₃₇O—(CH₂—CH₂O)₂]₂(EtO)Si(CH₂)₃SH,
[(C₁₈H₃₇O—(CH₂—CH₂O)₃]₂(EtO)Si(CH₂)₃SH,
[(C₁₈H₃₇O—(CH₂—CH₂O)₄]₂(EtO)Si(CH₂)₃SH,
[(C₁₈H₃₇O—(CH₂—CH₂O)₅]₂(EtO)Si(CH₂)₃SH,
[(C₁₈H₃₇O—(CH₂—CH₂O)₆]₂(EtO)Si(CH₂)₃SH,
[(C₄H₉O—(CH₂—CH₂O)₂]₃Si(CH₂)₃SH,
[(C₄H₉O—(CH₂—CH₂O)₃]₃Si(CH₂)₃SH,
[(C₄H₉O—(CH₂—CH₂O)₄]₃Si(CH₂)₃SH,
[(C₄H₉O—(CH₂—CH₂O)₅]₃Si(CH₂)₃SH,
[(C₄H₉O—(CH₂—CH₂O)₆]₃Si(CH₂)₃SH,
[(C₆H₁₃O—(CH₂—CH₂O)₂]₃Si(CH₂)₃SH,
[(C₆H₁₃O—(CH₂—CH₂O)₃]₃Si(CH₂)₃SH,
[(C₆H₁₃O—(CH₂—CH₂O)₄]₃Si(CH₂)₃SH,
[(C₆H₁₃O—(CH₂—CH₂O)₅]₃Si(CH₂)₃SH,
[(C₆H₁₃O—(CH₂—CH₂O)₆]₃Si(CH₂)₃SH,
[(C₈H₁₇O—(CH₂—CH₂O)₂]₃Si(CH₂)₃SH,
[(C₈H₁₇O—(CH₂—CH₂O)₃]₃Si(CH₂)₃SH,
[(C₈H₁₇O—(CH₂—CH₂O)₄]₃Si(CH₂)₃SH,
[(C₈H₁₇O—(CH₂—CH₂O)₅]₃Si(CH₂)₃SH,
[(C₈H₁₇O—(CH₂—CH₂O)₆]₃Si(CH₂)₃SH,
[(C₉H₁₉O—(CH₂—CH₂O)₂]₃Si(CH₂)₃SH,
[(C₉H₁₉O—(CH₂—CH₂O)₃]₃Si(CH₂)₃SH,
[(C₉H₁₉O—(CH₂—CH₂O)₄]₃Si(CH₂)₃SH,
[(C₉H₁₉O—(CH₂—CH₂O)₅]₃Si(CH₂)₃SH,
[(C₉H₁₉O—(CH₂—CH₂O)₆]₃Si(CH₂)₃SH,
[(C₁₀H₂₁O—(CH₂—CH₂O)₂]₃Si(CH₂)₃SH,
[(C₁₀H₂₁O—(CH₂—CH₂O)₃]₃Si(CH₂)₃SH,
[(C₁₀H₂₁O—(CH₂—CH₂O)₄]₃Si(CH₂)₃SH,
[(C₁₀H₂₁O—(CH₂—CH₂O)₅]₃Si(CH₂)₃SH,
[(C₁₀H₂₁O—(CH₂—CH₂O)₆]₃Si(CH₂)₃SH,
[(C₁₂H₂₅O—(CH₂—CH₂O)₂]₃Si(CH₂)₃SH,
[(C₁₂H₂₅O—(CH₂—CH₂O)₃]₃Si(CH₂)₃SH,
[(C₁₂H₂₅O—(CH₂—CH₂O)₄]₃Si(CH₂)₃SH,
[(C₁₂H₂₅O—(CH₂—CH₂O)₅]₃Si(CH₂)₃SH,
[(C₁₂H₂₅O—(CH₂—CH₂O)₆]₃Si(CH₂)₃SH,
[(C₁₃H₂₇O—(CH₂—CH₂O)₂]₃Si(CH₂)₃SH,
[(C₁₃H₂₇O—(CH₂—CH₂O)₃]₃Si(CH₂)₃SH,
[(C₁₃H₂₇O—(CH₂—CH₂O)₄]₃Si(CH₂)₃SH,
[(C₁₃H₂₇O—(CH₂—CH₂O)₅]₃Si(CH₂)₃SH,
[(C₁₃H₂₇O—(CH₂—CH₂O)₆]₃Si(CH₂)₃SH,
[(C₁₄H₂₉O—(CH₂—CH₂O)₂]₃Si(CH₂)₃SH,
[(C₁₄H₂₉O—(CH₂—CH₂O)₃]₃Si(CH₂)₃SH,
[(C₁₄H₂₉O—(CH₂—CH₂O)₄]₃Si(CH₂)₃SH,
[(C₁₄H₂₉O—(CH₂—CH₂O)₅]₃Si(CH₂)₃SH,
[(C₁₄H₂₉O—(CH₂—CH₂O)₆]₃Si(CH₂)₃SH,
[(C₁₅H₃₁O—(CH₂—CH₂O)₂]₃Si(CH₂)₃SH,
[(C₁₅H₃₁O—(CH₂—CH₂O)₃]₃Si(CH₂)₃SH,
[(C₁₅H₃₁O—(CH₂—CH₂O)₄]₃Si(CH₂)₃SH,
[(C₁₅H₃₁O—(CH₂—CH₂O)₅]₃Si(CH₂)₃SH,
[(C₁₅H₃₁O—(CH₂—CH₂O)₆]₃Si(CH₂)₃SH,
[(C₁₆H₃₃O—(CH₂—CH₂O)₂]₃Si(CH₂)₃SH,
[(C₁₆H₃₃O—(CH₂—CH₂O)₃]₃Si(CH₂)₃SH,
[(C₁₆H₃₃O—(CH₂—CH₂O)₄]₃Si(CH₂)₃SH,
[(C₁₆H₃₃O—(CH₂—CH₂O)₅]₃Si(CH₂)₃SH,
[(C₁₆H₃₃O—(CH₂—CH₂O)₆]₃Si(CH₂)₃SH,
[(C₁₈H₃₇O—(CH₂—CH₂O)₂]₃Si(CH₂)₃SH,
[(C₁₈H₃₇O—(CH₂—CH₂O)₃]₃Si(CH₂)₃SH,
[(C₁₈H₃₇O—(CH₂—CH₂O)₄]₃Si(CH₂)₃SH,
[(C₁₈H₃₇O—(CH₂—CH₂O)₅]₃Si(CH₂)₃SH or
[(C₁₈H₃₇O—(CH₂—CH₂O)₆]₃Si(CH₂)₃SH, where the alkyl radicals may be unbranched or branched.

Compounds of the formula I where Alk=$C_3H_7$, $C_4H_9$, $C_5H_{11}$, $C_6H_{13}$, $C_7H_{15}$, $C_8H_{17}$, $C_9H_{19}$, $C_{10}H_{21}$, $C_{11}H_{23}$, $C_{12}H_{25}$, $C_{13}H_{27}$, $C_{14}H_{29}$, $C_{15}H_{31}$, $C_{16}H_{33}$, $C_{17}H_{35}$, $C_{18}H_{37}$, $C_{19}H_{39}$ or $C_{20}H_{41}$ may be:

[(Alk-O—(CH₂—CH(CH₃)O—)₂](MeO)₂Si(CH₂)₃SH,
[(Alk-O—(CH₂—CH(CH₃)O—)₃](MeO)₂Si(CH₂)₃SH,
[(Alk-O—(CH₂—CH(CH₃)O—)₄](MeO)₂Si(CH₂)₃SH,
[(Alk-O—(CH₂—CH(CH₃)O—)₅](MeO)₂Si(CH₂)₃SH,
[(Alk-O—(CH₂—CH(CH₃)O—)₆](MeO)₂Si(CH₂)₃SH,
[(Alk-O—(CH₂—CH(CH₃)O—)₇](MeO)₂Si(CH₂)₃SH,
[(Alk-O—(CH₂—CH(CH₃)O—)₈](MeO)₂Si(CH₂)₃SH,
[(Alk-O—(CH₂—CH(CH₃)O—)₉](MeO)₂Si(CH₂)₃SH,
[(Alk-O—(CH₂—CH(CH₃)O—)₁₀](MeO)₂Si(CH₂)₃SH,
[(Alk-O—(CH₂—CH(CH₃)O—)₁₁](MeO)₂Si(CH₂)₃SH,
[(Alk-O—(CH₂—CH(CH₃)O—)₁₂](MeO)₂Si(CH₂)₃SH,
[(Alk-O—(CH₂—CH(CH₃)O—)₁₃](MeO)₂Si(CH₂)₃SH,
[(Alk-O—(CH₂—CH(CH₃)O—)₁₄](MeO)₂Si(CH₂)₃SH,
[(Alk-O—(CH₂—CH(CH₃)O—)₁₅](MeO)₂Si(CH₂)₃SH,
[(Alk-O—(CH₂—CH(CH₃)O—)₁₆](MeO)₂Si(CH₂)₃SH,
[(Alk-O—(CH₂—CH(CH₃)O—)₁₇](MeO)₂Si(CH₂)₃SH,
[(Alk-O—(CH₂—CH(CH₃)O—)₁₈](MeO)₂Si(CH₂)₃SH,
[(Alk-O—(CH₂—CH(CH₃)O—)₁₉](MeO)₂Si(CH₂)₃SH,
[(Alk-O—(CH₂—CH(CH₃)O—)₂₀](MeO)₂Si(CH₂)₃SH,
[(Alk-O—(CH₂—CH(CH₃)O—)₂]₂(MeO)Si(CH₂)₃SH,
[(Alk-O—(CH₂—CH(CH₃)O—)₃]₂(MeO)Si(CH₂)₃SH,
[(Alk-O—(CH₂—CH(CH₃)O—)₄]₂(MeO)Si(CH₂)₃SH,
[(Alk-O—(CH₂—CH(CH₃)O—)₅]₂(MeO)Si(CH₂)₃SH,
[(Alk-O—(CH₂—CH(CH₃)O—)₆]₂(MeO)Si(CH₂)₃SH,

[(Alk-O—(CH$_2$—CH(CH$_3$)O—)$_7$]$_2$(MeO)Si(CH$_2$)$_3$SH,
[(Alk-O—(CH$_2$—CH(CH$_3$)O—)$_8$]$_2$(MeO)Si(CH$_2$)$_3$SH,
[(Alk-O—(CH$_2$—CH(CH$_3$)O—)$_9$]$_2$(MeO)Si(CH$_2$)$_3$SH,
[(Alk-O—(CH$_2$—CH(CH$_3$)O—)$_{10}$]$_2$(MeO)Si(CH$_2$)$_3$SH,
[(Alk-O—(CH$_2$—CH(CH$_3$)O—)$_{11}$]$_2$(MeO)Si(CH$_2$)$_3$SH,
[(Alk-O—(CH$_2$—CH(CH$_3$)O—)$_{12}$]$_2$(MeO)Si(CH$_2$)$_3$SH,
[(Alk-O—(CH$_2$—CH(CH$_3$)O—)$_{13}$]$_2$(MeO)Si(CH$_2$)$_3$SH,
[(Alk-O—(CH$_2$—CH(CH$_3$)O—)$_{14}$]$_2$(MeO)Si(CH$_2$)$_3$SH,
[(Alk-O—(CH$_2$—CH(CH$_3$)O—)$_{15}$]$_2$(MeO)Si(CH$_2$)$_3$SH,
[(Alk-O—(CH$_2$—CH(CH$_3$)O—)$_{16}$]$_2$(MeO)Si(CH$_2$)$_3$SH,
[(Alk-O—(CH$_2$—CH(CH$_3$)O—)$_{17}$]$_2$(MeO)Si(CH$_2$)$_3$SH,
[(Alk-O—(CH$_2$—CH(CH$_3$)O—)$_{18}$]$_2$(MeO)Si(CH$_2$)$_3$SH,
[(Alk-O—(CH$_2$—CH(CH$_3$)O—)$_{19}$]$_2$(MeO)Si(CH$_2$)$_3$SH,
[(Alk-O—(CH$_2$—CH(CH$_3$)O—)$_{20}$]$_2$(MeO)Si(CH$_2$)$_3$SH,
[(Alk-O—(CH$_2$—CH(CH$_3$)O—)$_2$](Me)(MeO)Si(CH$_2$)$_3$SH,
[(Alk-O—(CH$_2$—CH(CH$_3$)O—)$_3$](Me)(MeO)Si(CH$_2$)$_3$SH,
[(Alk-O—(CH$_2$—CH(CH$_3$)O—)$_4$](Me)(MeO)Si(CH$_2$)$_3$SH,
[(Alk-O—(CH$_2$—CH(CH$_3$)O—)$_5$](Me)(MeO)Si(CH$_2$)$_3$SH,
[(Alk-O—(CH$_2$—CH(CH$_3$)O—)$_6$](Me)(MeO)Si(CH$_2$)$_3$SH,
[(Alk-O—(CH$_2$—CH(CH$_3$)O—)$_7$](Me)(MeO)Si(CH$_2$)$_3$SH,
[(Alk-O—(CH$_2$—CH(CH$_3$)O—)$_8$](Me)(MeO)Si(CH$_2$)$_3$SH,
[(Alk-O—(CH$_2$—CH(CH$_3$)O—)$_9$](Me)(MeO)Si(CH$_2$)$_3$SH,
[(Alk-O—(CH$_2$—CH(CH$_3$)O—)$_{10}$](Me)(MeO)Si(CH$_2$)$_3$SH,
[(Alk-O—(CH$_2$—CH(CH$_3$)O—)$_{11}$](Me)(MeO)Si(CH$_2$)$_3$SH,
[(Alk-O—(CH$_2$—CH(CH$_3$)O—)$_{12}$](Me)(MeO)Si(CH$_2$)$_3$SH,
[(Alk-O—(CH$_2$—CH(CH$_3$)O—)$_{13}$](Me)(MeO)Si(CH$_2$)$_3$SH,
[(Alk-O—(CH$_2$—CH(CH$_3$)O—)$_{14}$](Me)(MeO)Si(CH$_2$)$_3$SH,
[(Alk-O—(CH$_2$—CH(CH$_3$)O—)$_{15}$](Me)(MeO)Si(CH$_2$)$_3$SH,
[(Alk-O—(CH$_2$—CH(CH$_3$)O—)$_{16}$](Me)(MeO)Si(CH$_2$)$_3$SH,
[(Alk-O—(CH$_2$—CH(CH$_3$)O—)$_{17}$](Me)(MeO)Si(CH$_2$)$_3$SH,
[(Alk-O—(CH$_2$—CH(CH$_3$)O—)$_{18}$](Me)(MeO)Si(CH$_2$)$_3$SH,
[(Alk-O—(CH$_2$—CH(CH$_3$)O—)$_{19}$](Me)(MeO)Si(CH$_2$)$_3$SH,
[(Alk-O—(CH$_2$—CH(CH$_3$)O—)$_{20}$](Me)(MeO)Si(CH$_2$)$_3$SH,
[(Alk-O—(CH$_2$—CH(CH$_3$)O—)$_2$](EtO)$_2$Si(CH$_2$)$_3$SH,
[(Alk-O—(CH$_2$—CH(CH$_3$)O—)$_3$](EtO)$_2$Si(CH$_2$)$_3$SH,
[(Alk-O—(CH$_2$—CH(CH$_3$)O—)$_4$](EtO)$_2$Si(CH$_2$)$_3$SH,
[(Alk-O—(CH$_2$—CH(CH$_3$)O—)$_5$](EtO)$_2$Si(CH$_2$)$_3$SH,
[(Alk-O—(CH$_2$—CH(CH$_3$)O—)$_6$](EtO)$_2$Si(CH$_2$)$_3$SH,
[(Alk-O—(CH$_2$—CH(CH$_3$)O—)$_7$](EtO)$_2$Si(CH$_2$)$_3$SH,
[(Alk-O—(CH$_2$—CH(CH$_3$)O—)$_8$](EtO)$_2$Si(CH$_2$)$_3$SH,
[(Alk-O—(CH$_2$—CH(CH$_3$)O—)$_9$](EtO)$_2$Si(CH$_2$)$_3$SH,
[(Alk-O—(CH$_2$—CH(CH$_3$)O—)$_{10}$](EtO)$_2$Si(CH$_2$)$_3$SH,
[(Alk-O—(CH$_2$—CH(CH$_3$)O—)$_{11}$](EtO)$_2$Si(CH$_2$)$_3$SH,
[(Alk-O—(CH$_2$—CH(CH$_3$)O—)$_{12}$](EtO)$_2$Si(CH$_2$)$_3$SH,
[(Alk-O—(CH$_2$—CH(CH$_3$)O—)$_{13}$](EtO)$_2$Si(CH$_2$)$_3$SH,
[(Alk-O—(CH$_2$—CH(CH$_3$)O—)$_{14}$](EtO)$_2$Si(CH$_2$)$_3$SH,
[(Alk-O—(CH$_2$—CH(CH$_3$)O—)$_{15}$](EtO)$_2$Si(CH$_2$)$_3$SH,
[(Alk-O—(CH$_2$—CH(CH$_3$)O—)$_{16}$](EtO)$_2$Si(CH$_2$)$_3$SH,
[(Alk-O—(CH$_2$—CH(CH$_3$)O—)$_{17}$](EtO)$_2$Si(CH$_2$)$_3$SH,
[(Alk-O—(CH$_2$—CH(CH$_3$)O—)$_{18}$](EtO)$_2$Si(CH$_2$)$_3$SH,
[(Alk-O—(CH$_2$—CH(CH$_3$)O—)$_{19}$](EtO)$_2$Si(CH$_2$)$_3$SH,
[(Alk-O—(CH$_2$—CH(CH$_3$)O—)$_{20}$](EtO)$_2$Si(CH$_2$)$_3$SH,
[(Alk-O—(CH$_2$—CH(CH$_3$)O—)$_2$]$_2$(EtO)Si(CH$_2$)$_3$SH,
[(Alk-O—(CH$_2$—CH(CH$_3$)O—)$_3$]$_2$(EtO)Si(CH$_2$)$_3$SH,
[(Alk-O—(CH$_2$—CH(CH$_3$)O—)$_4$]$_2$(EtO)Si(CH$_2$)$_3$SH,
[(Alk-O—(CH$_2$—CH(CH$_3$)O—)$_5$]$_2$(EtO)Si(CH$_2$)$_3$SH,
[(Alk-O—(CH$_2$—CH(CH$_3$)O—)$_6$]$_2$(EtO)Si(CH$_2$)$_3$SH,
[(Alk-O—(CH$_2$—CH(CH$_3$)O—)$_7$]$_2$(EtO)Si(CH$_2$)$_3$SH,
[(Alk-O—(CH$_2$—CH(CH$_3$)O—)$_8$]$_2$(EtO)Si(CH$_2$)$_3$SH,
[(Alk-O—(CH$_2$—CH(CH$_3$)O—)$_9$]$_2$(EtO)Si(CH$_2$)$_3$SH,
[(Alk-O—(CH$_2$—CH(CH$_3$)O—)$_{10}$]$_2$(EtO)Si(CH$_2$)$_3$SH,
[(Alk-O—(CH$_2$—CH(CH$_3$)O—)$_{11}$]$_2$(EtO)Si(CH$_2$)$_3$SH,
[(Alk-O—(CH$_2$—CH(CH$_3$)O—)$_{12}$]$_2$(EtO)Si(CH$_2$)$_3$SH,
[(Alk-O—(CH$_2$—CH(CH$_3$)O—)$_{13}$]$_2$(EtO)Si(CH$_2$)$_3$SH,
[(Alk-O—(CH$_2$—CH(CH$_3$)O—)$_{14}$]$_2$(EtO)Si(CH$_2$)$_3$SH,
[(Alk-O—(CH$_2$—CH(CH$_3$)O—)$_{15}$]$_2$(EtO)Si(CH$_2$)$_3$SH,
[(Alk-O—(CH$_2$—CH(CH$_3$)O—)$_{16}$]$_2$(EtO)Si(CH$_2$)$_3$SH,
[(Alk-O—(CH$_2$—CH(CH$_3$)O—)$_{17}$]$_2$(EtO)Si(CH$_2$)$_3$SH,
[(Alk-O—(CH$_2$—CH(CH$_3$)O—)$_{18}$]$_2$(EtO)Si(CH$_2$)$_3$SH,
[(Alk-O—(CH$_2$—CH(CH$_3$)O—)$_{19}$]$_2$(EtO)Si(CH$_2$)$_3$SH,
[(Alk-O—(CH$_2$—CH(CH$_3$)O—)$_{20}$]$_2$(EtO)Si(CH$_2$)$_3$SH,
[(Alk-O—(CH$_2$—CH(CH$_3$)O—)$_2$](Me)(EtO)Si(CH$_2$)$_3$SH,
[(Alk-O—(CH$_2$—CH(CH$_3$)O—)$_3$](Me)(EtO)Si(CH$_2$)$_3$SH,
[(Alk-O—(CH$_2$—CH(CH$_3$)O—)$_4$](Me)(EtO)Si(CH$_2$)$_3$SH,
[(Alk-O—(CH$_2$—CH(CH$_3$)O—)$_5$](Me)(EtO)Si(CH$_2$)$_3$SH,
[(Alk-O—(CH$_2$—CH(CH$_3$)O—)$_6$](Me)(EtO)Si(CH$_2$)$_3$SH,
[(Alk-O—(CH$_2$—CH(CH$_3$)O—)$_7$](Me)(EtO)Si(CH$_2$)$_3$SH,
[(Alk-O—(CH$_2$—CH(CH$_3$)O—)$_8$](Me)(EtO)Si(CH$_2$)$_3$SH,
[(Alk-O—(CH$_2$—CH(CH$_3$)O—)$_9$](Me)(EtO)Si(CH$_2$)$_3$SH,
[(Alk-O—(CH$_2$—CH(CH$_3$)O—)$_{10}$](Me)(EtO)Si(CH$_2$)$_3$SH,
[(Alk-O—(CH$_2$—CH(CH$_3$)O—)$_{11}$](Me)(EtO)Si(CH$_2$)$_3$SH,
[(Alk-O—(CH$_2$—CH(CH$_3$)O—)$_{12}$](Me)(EtO)Si(CH$_2$)$_3$SH,
[(Alk-O—(CH$_2$—CH(CH$_3$)O—)$_{13}$](Me)(EtO)Si(CH$_2$)$_3$SH,
[(Alk-O—(CH$_2$—CH(CH$_3$)O—)$_{14}$](Me)(EtO)Si(CH$_2$)$_3$SH,
[(Alk-O—(CH$_2$—CH(CH$_3$)O—)$_{15}$](Me)(EtO)Si(CH$_2$)$_3$SH,
[(Alk-O—(CH$_2$—CH(CH$_3$)O—)$_{16}$](Me)(EtO)Si(CH$_2$)$_3$SH,
[(Alk-O—(CH$_2$—CH(CH$_3$)O—)$_{17}$](Me)(EtO)Si(CH$_2$)$_3$SH,
[(Alk-O—(CH$_2$—CH(CH$_3$)O—)$_{18}$](Me)(EtO)Si(CH$_2$)$_3$SH,
[(Alk-O—(CH$_2$—CH(CH$_3$)O—)$_{19}$](Me)(EtO)Si(CH$_2$)$_3$SH,
[(Alk-O—(CH$_2$—CH(CH$_3$)O—)$_{20}$](Me)(EtO)Si(CH$_2$)$_3$SH,
[(Alk-O—(CH$_2$—CH(CH$_3$)O—)$_2$]$_2$(Me)Si(CH$_2$)$_3$SH,
[(Alk-O—(CH$_2$—CH(CH$_3$)O—)$_3$]$_2$(Me)Si(CH$_2$)$_3$SH,
[(Alk-O—(CH$_2$—CH(CH$_3$)O—)$_4$]$_2$(Me)Si(CH$_2$)$_3$SH,
[(Alk-O—(CH$_2$—CH(CH$_3$)O—)$_5$]$_2$(Me)Si(CH$_2$)$_3$SH,
[(Alk-O—(CH$_2$—CH(CH$_3$)O—)$_6$]$_2$(Me)Si(CH$_2$)$_3$SH,
[(Alk-O—(CH$_2$—CH(CH$_3$)O—)$_7$]$_2$(Me)Si(CH$_2$)$_3$SH,
[(Alk-O—(CH$_2$—CH(CH$_3$)O—)$_8$]$_2$(Me)Si(CH$_2$)$_3$SH,
[(Alk-O—(CH$_2$—CH(CH$_3$)O—)$_9$]$_2$(Me)Si(CH$_2$)$_3$SH,
[(Alk-O—(CH$_2$—CH(CH$_3$)O—)$_{10}$]$_2$(Me)Si(CH$_2$)$_3$SH,
[(Alk-O—(CH$_2$—CH(CH$_3$)O—)$_{11}$]$_2$(Me)Si(CH$_2$)$_3$SH,
[(Alk-O—(CH$_2$—CH(CH$_3$)O—)$_{12}$]$_2$(Me)Si(CH$_2$)$_3$SH,
[(Alk-O—(CH$_2$—CH(CH$_3$)O—)$_{13}$]$_2$(Me)Si(CH$_2$)$_3$SH,
[(Alk-O—(CH$_2$—CH(CH$_3$)O—)$_{14}$]$_2$(Me)Si(CH$_2$)$_3$SH,
[(Alk-O—(CH$_2$—CH(CH$_3$)O—)$_{15}$]$_2$(Me)Si(CH$_2$)$_3$SH,
[(Alk-O—(CH$_2$—CH(CH$_3$)O—)$_{16}$]$_2$(Me)Si(CH$_2$)$_3$SH,
[(Alk-O—(CH$_2$—CH(CH$_3$)O—)$_{17}$]$_2$(Me)Si(CH$_2$)$_3$SH,
[(Alk-O—(CH$_2$—CH(CH$_3$)O—)$_{18}$]$_2$(Me)Si(CH$_2$)$_3$SH,
[(Alk-O—(CH$_2$—CH(CH$_3$)O—)$_{19}$]$_2$(Me)Si(CH$_2$)$_3$SH,
[(Alk-O—(CH$_2$—CH(CH$_3$)O—)$_{20}$]$_2$(Me)Si(CH$_2$)$_3$SH,
[(Alk-O—(CH$_2$—CH(CH$_3$)O—)$_2$](Me)$_2$Si(CH$_2$)$_3$SH,
[(Alk-O—(CH$_2$—CH(CH$_3$)O—)$_3$](Me)$_2$Si(CH$_2$)$_3$SH,
[(Alk-O—(CH$_2$—CH(CH$_3$)O—)$_4$](Me)$_2$Si(CH$_2$)$_3$SH,
[(Alk-O—(CH$_2$—CH(CH$_3$)O—)$_5$](Me)$_2$Si(CH$_2$)$_3$SH,
[(Alk-O—(CH$_2$—CH(CH$_3$)O—)$_6$](Me)$_2$Si(CH$_2$)$_3$SH,
[(Alk-O—(CH$_2$—CH(CH$_3$)O—)$_7$](Me)$_2$Si(CH$_2$)$_3$SH,
[(Alk-O—(CH$_2$—CH(CH$_3$)O—)$_8$](Me)$_2$Si(CH$_2$)$_3$SH,
[(Alk-O—(CH$_2$—CH(CH$_3$)O—)$_9$](Me)$_2$Si(CH$_2$)$_3$SH,
[(Alk-O—(CH$_2$—CH(CH$_3$)O—)$_{10}$](Me)$_2$Si(CH$_2$)$_3$SH,
[(Alk-O—(CH$_2$—CH(CH$_3$)O—)$_{11}$](Me)$_2$Si(CH$_2$)$_3$SH,
[(Alk-O—(CH$_2$—CH(CH$_3$)O—)$_{12}$](Me)$_2$Si(CH$_2$)$_3$SH,
[(Alk-O—(CH$_2$—CH(CH$_3$)O—)$_{13}$](Me)$_2$Si(CH$_2$)$_3$SH,
[(Alk-O—(CH$_2$—CH(CH$_3$)O—)$_{14}$](Me)$_2$Si(CH$_2$)$_3$SH,
[(Alk-O—(CH$_2$—CH(CH$_3$)O—)$_{15}$](Me)$_2$Si(CH$_2$)$_3$SH,

[(Alk-O—(CH$_2$—CH(CH$_3$)O—)$_{16}$](Me)$_2$Si(CH$_2$)$_3$SH,
[(Alk-O—(CH$_2$—CH(CH$_3$)O—)$_{17}$](Me)$_2$Si(CH$_2$)$_3$SH,
[(Alk-O—(CH$_2$—CH(CH$_3$)O—)$_{18}$](Me)$_2$Si(CH$_2$)$_3$SH,
[(Alk-O—(CH$_2$—CH(CH$_3$)O—)$_{19}$](Me)$_2$Si(CH$_2$)$_3$SH or
[(Alk-O—(CH$_2$—CH(CH$_3$)O—)$_{20}$](Me)$_2$Si(CH$_2$)$_3$SH, where the Alk groups may be unbranched or branched.

The (haloorganyl)alkyl polyether silanes used may be compounds of the general formula II $$(X)(X')(X'')Si—R^I-Hal \qquad II$$

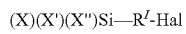

where $R^I$, X, X' and X'' are each as defined above and Hal is chlorine, bromine, fluorine or iodine.

The (haloorganyl)alkyl polyether silanes used may preferably be those which arise from the (mercaptoorganyl)alkyl polyether silanes listed above by the formal exchange of the HS-substituent for Hal-.

The (haloorganyl)alkyl polyether silane may be a (haloorganyl)alkyl polyether silane of the formula II or a mixture of (haloorganyl)alkyl polyether silanes of the formula II.

Mercaptation reagents are compounds which can convert a halogen-C bond in a hydrocarbon to an HS—C bond.

The dry mercaptation reagents may have a water content of less than 2.5% by weight, preferably less than 2% by weight, more preferably less than 1% by weight, even more preferably less than 0.5% by weight, exceptionally preferably less than 0.2% by weight.

The water content of solid mercaptation reagents can be determined as follows: For the determination of water content, glass beads are moistened slightly, covered with phosphorus pentoxide and then filled into a U-tube. Approx. 3 g of the sample are weighed into a 50 ml flask, baked out at 320° C. under a nitrogen stream (30 ml/min) dried with Sicapent for 2 hours, and then left to stand under a nitrogen stream for another 30 min. The moist carrier gas is passed through a hose connection from the flask into the U-tube. Possible condensation between flask and U-tube is driven out during the baking-out phase with the aid of a hot air gun. The U-tube is weighed again and the amount of water released from the sulfuration reagents is determined gravimetrically.

The water content of mercaptation reagents formed in situ, for example from H$_2$S and alkali metal alkoxides, can be determined by water determination in the reactants used for this purpose, for example the H$_2$S and the alkali metal alkoxide.

The water content of mercaptation reagents formed in situ, for example from H$_2$S and the solid dry Na$_2$S reagent, can be determined by water determination in the reactants used for this purpose, for example the H$_2$S and the solid dry Na$_2$S.

The water content of mercaptation reagents formed in situ, for example ammonium hydrogensulfide from H$_2$S and amine, can be determined by water determination in the reactants used for this purpose, for example the H$_2$S and amine.

The dry mercaptation reagents required for the reaction may be alkali metal hydrogensulfide or ammonium hydrogensulfide.

The mercaptation reagent used may contain no urea derivatives or thiourea derivatives, or be formed therefrom.

The dry alkali metal hydrogensulfide used may be lithium hydrogensulfide (LiSH), sodium hydrogensulfide (NaSH), potassium hydrogensulfide (KSH) and cesium hydrogensulfide (CsSH).

The dry ammonium hydrogensulfide used may be (NH$_4$)SH, NH$_3$(Sub)SH, NH$_2$(Sub)$_2$SH or NH(Sub)$_3$SH, where Sub is a branched or unbranched, saturated or unsaturated, aliphatic, aromatic or mixed aliphatic/aromatic monovalent C$_1$-C$_{30}$-hydrocarbon group, preferably C$_1$-C$_{25}$-hydrocarbon group, more preferably C$_2$-C$_{20}$-hydrocarbon group, even more preferably C$_3$-C$_{16}$-hydrocarbon group, exceptionally preferably C$_{11}$-C$_{25}$-hydrocarbon group. The Sub group may be CH$_3$, CH$_2$—CH$_3$, i-propyl, n-propyl, n-butyl, i-butyl, t-butyl, pentyl or phenyl.

The molar amount of dry mercaptation reagent used may, based on the amount of the (haloorganyl)alkyl polyether silane used, be from 70 mol % to 150 mol %, preferably from 90 mol % to 125 mol %, more preferably from 95 mol % to 115 mol %, exceptionally preferably from 100 to 110 mol %.

Smaller than equimolar amounts of dry mercaptation reagents may lead to incomplete conversion. As a result, the product may subsequently either be contaminated with reactants, or a complicated purification, for example distillation, becomes necessary under some circumstances in order to separate reactants and products from one another.

The dry mercaptation reagents required for the reaction can be formed before or during the reaction.

The formation of the dry mercaptation reagents required may be completed before the reaction with the (haloorganyl) alkyl polyether silane.

The dry alkali metal hydrogensulfides may be formed from water-containing alkali metal hydrogensulfides by drying. The drying may be an azeotropic drying, drying with infrared light, drying with microwaves, drying at elevated temperature, drying under reduced pressure, drying at elevated temperature and reduced pressure, or drying at reduced temperature (freeze-drying).

The dry mercaptation reagents required for the reaction can be formed from alkoxides and H$_2$S before or during the reaction.

The alkoxides may be alkali metal alkoxides. Alkoxide may be mixtures of alkali metal alkoxides.

Preferred alkali metal alkoxides may be Na(O-Alk), Li(O-Alk), K(O-Alk), NaO-(CR$^{II}_2$—CR$^{II}_2$—O)$_v$-Alk, LiO-(CR$^{II}_2$—CR$^{II}_2$—O)$_v$-Alk and KO—(CR$^{II}_2$—CR$^{II}_2$—O)$_v$-Alk. Particularly preferred alkali metal alkoxides may be Na—OMe, Na—OEt, Na—OC$_3$H$_7$, Na—O—C$_4$H$_9$, Li—OMe, Li—OEt, Li—OC$_3$H$_7$, Li—O—C$_4$H$_9$, K-OMe, K-OEt, K—OC$_3$H$_7$ or K—O—C$_4$H$_9$.

The dry mercaptation reagents required for the reaction can be formed from dry alkali metal sulfide and H$_2$S before or during the reaction. Preferred alkali metal sulfides are Li$_2$S, Na$_2$S or K$_2$S.

The dry alkali metal sulfides can be formed from alkoxides and H$_2$S.

The dry alkali metal sulfides can be formed from water-containing alkali metal sulfides by drying. The drying may be an azeotropic drying, drying with infrared light, drying with microwaves, drying at elevated temperature, drying at reduced pressure, drying at elevated temperature and reduced pressure, or drying at reduced temperature (freeze-drying).

The dry mercaptation reagents required for the reaction may be formed from aqueous mercaptation reagents and desiccants before or during the reaction.

Desiccants may be halosilanes or alkoxysilanes.

The dry mercaptation reagents required for the reaction may be formed from water-containing mercaptation reagents and halosilanes before or during the reaction.

Halosilanes may contain 1, 2, 3 or 4 Hal bonds per silicon atom. Halosilanes may be chlorosilanes. Chlorosilanes may be (CH$_3$)SiCl$_3$, (CH$_3$)$_2$SiCl$_2$, (CH$_3$)$_3$SiCl, SiCl$_4$, (CH$_3$CH$_2$CH$_2$)SiCl$_3$, (Cl—CH$_2$CH$_2$CH$_2$)SiCl$_3$, (Cl—CH$_2$CH$_2$CH$_2$)SiCl$_2$(OMe), (Cl—CH$_2$CH$_2$CH$_2$)SiCl$_2$(OEt), (Cl—CH$_2$CH$_2$CH$_2$)SiCl$_2$(X), (Cl—CH$_2$CH$_2$CH$_2$)SiCl(OMe)$_2$, (Cl—CH$_2$CH$_2$CH$_2$)SiCl(OEt)$_2$, (Cl—CH$_2$CH$_2$CH$_2$)SiCl(X)$_2$, HSiCl$_3$ or H$_2$SiCl$_2$.

Halosilanes may be mixtures of different halosilanes.

The dry mercaptation reagents required for the reaction can be formed from water-containing mercaptation reagents and alkoxysilanes before or during the reaction.

Alkoxysilanes may contain 1, 2, 3 or 4 (—O-Sub) substituents per silicon atom. Alkoxysilanes may be methoxysilanes, ethoxysilanes, propoxy- or butoxysilanes. Alkoxysilanes may be $(CH_3)Si(OMe)_3$, $(CH_3)_2Si(OMe)_2$, $(CH_3)_3SiOMe$, $SiOMe_4$, $(CH_3CH_2CH_2)Si(OMe)_3$, $(Cl—CH_2CH_2CH_2)Si(OMe)_3$, $(CH_3)Si(OEt)_3$, $(CH_3)_2Si(OEt)_2$, $(CH_3)_3SiOEt$, $SiOEt_4$, $(CH_3CH_2CH_2)Si(OEt)_3$, $(Cl—CH_2CH_2CH_2)Si(OEt)_3$, $Si(OC_3H_7)_4$, $Si(OC_4H_9)_4$, $(Cl—CH_2CH_2CH_2)SiCl_2(OMe)$, $(Cl—CH_2CH_2CH_2)SiCl_2(OEt)$, $(Cl—CH_2CH_2CH_2)SiCl_2(X)$, $(Cl—CH_2CH_2CH_2)SiCl(OMe)_2$, $(Cl—CH_2CH_2CH_2)SiCl(OEt)_2$ or $(Cl—CH_2CH_2CH_2)SiCl(X)_2$.

Alkoxysilanes may be mixtures of different alkoxysilanes.

The dry mercaptation reagents required for the reaction may be formed from amines and $H_2S$ before or during the reaction. Amines may be $(Sub)-NH_2$, $(Sub)_2NH$, $(Sub)_3N$. Amines may preferably be $NH_3$, $CH_3—NH_2$, $(CH_3)_2NH$, $(CH_3)_3N$, $CH_3CH_2—NH_2$, $(CH_3CH_2)_2NH$, $(CH_3CH_2)_3N$ or $C_6H_5—NH_2$.

The protonation of reactant compounds, from which alkali metal hydrogensulfide or ammonium hydrogensulfide is formed before or during the reaction, can be effected by $H_2S$ and/or organic and/or inorganic acids.

The deprotonation of the reactant compounds, from which alkali metal hydrogensulfide or ammonium hydrogensulfide can be formed before or during the reaction, can be effected by organic and/or inorganic bases.

The reactant compound from which alkali metal hydrogensulfide can be formed by deprotonation may be $H_2S$.

The inorganic bases used for the deprotonation of $H_2S$ may, for example, be (alkali metal ion)$_2$HPO$_4$, (alkali metal ion)$_3$PO$_4$, (alkali metal ion)$_2$CO$_3$ or (alkali metal ion)$_2$SO$_4$. Preference may be given to using $Na_3PO_4$, $K_3PO_4$, $Na_2HPO_4$, $K_2HPO_4$, $K_2CO_3$, $Na_2CO_3$, $Na_2SO_4$ or $K_2SO_4$.

Before, during or after the reaction, additives may be added.

The additives used may preferably be, in pure or technical-grade quality, alkanes, for example pentane, hexane, cyclohexane, heptane or octane, ethers, for example diethyl ether, tetrahydrofuran, 1,2-dimethoxyethane, dioxane, dioxolane, ethylene glycols or propylene glycols, aromatics, for example benzene, toluene, o-xylene, m-xylene or p-xylene, or carbonyl compounds, for example dimethylformamide.

The additives used may be haloorganyl(halosilanes). The haloorganyl(halosilanes) used may be compounds of the general formulae III, IV or V

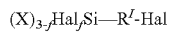  III

  IV

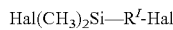  V where f is 1-3, h is 1 or 2,

X, Hal and $R^I$ are each as defined above.

The (haloorganyl)halosilanes used may preferably be 3-chlorobutyl(trichlorosilane), 3-chloropropyl(trichlorosilane), 3-chloro-2-methylpropyl(trichlorosilane), 2-chloroethyl(trichlorosilane), 1-chloromethyl(trichlorosilane), 3-chlorobutyl(dichloromethoxysilane), 3-chloropropyl(dichloromethoxysilane), 2-chloroethyl(dichloromethoxysilane), 1-chloromethyl(dichloromethoxysilane), 3-chlorobutyl(dichloroethoxysilane), 3-chloropropyl(dichloroethoxysilane), 2-chloroethyl(dichloroethoxysilane), 1-chloromethyl(dichloroethoxysilane), 3-chlorobutyl(chlorodiethoxysilane), 3-chloropropyl(chlorodiethoxysilane), 2-chloroethyl(chlorodiethoxysilane), 1-chloromethyl(chlorodiethoxysilane), 3-chlorobutyl(chlorodimethoxysilane), 3-chloropropyl(chlorodimethoxysilane), 2-chloroethyl(chlorodimethoxysilane), 1-chloromethyl(chlorodimethoxysilane), 3-chlorobutyl(dichloromethylsilane), 3-chloropropyl(dichloromethylsilane), 2-chloroethyl(dichloromethylsilane), 1-chloromethyl(dichloromethylsilane), 3-chlorobutyl(chloro-)(methyl-)methoxysilane, 3-chloropropyl(chloro-)(methyl-)methoxysilane, 2-chloroethyl(chloro-)(methyl-)methoxysilane, 1-chloromethyl(chloro-)(methyl-)methoxysilane, 3-chlorobutyl(chloro-)(methyl-)ethoxysilane, 3-chloropropyl(chloro-)(methyl-)ethoxysilane, 2-chloroethyl(chloro-)(methyl-)ethoxysilane, 1-chloromethyl(chloro-)(methyl-)ethoxysilane, 3-chlorobutyl(chlorodimethylsilane), 3-chloropropyl(chlorodimethylsilane), 2-chloroethyl(chlorodimethylsilane) or 1-chloromethyl(chlorodimethylsilane).

The (haloorganyl)halosilane may be a (haloorganyl)halosilane of the general formulae III, IV or V or a mixture of (haloorganyl)halosilanes of the general formulae III, IV or V.

At the start of the reaction and/or during the reaction and/or at the end of the reaction, polar, protic, aprotic, basic or acidic additives may be added to the reaction mixture.

Additives may, for example, be $H_2S$, (alkali metal ion)$H_2PO_4$, (alkali metal ion)$_2$HPO$_4$, (alkali metal ion)$_3$PO$_4$ (alkali metal ion)HCO$_3$, (alkali metal ion)$_2$CO$_3$, (alkali metal ion)$_2$SO$_4$ or (alkali metal ion)HSO$_4$. Preference may be given to using $KH_2PO_4$, $K_2HPO_4$, $KHCO_3$, $NaHCO_3$, $K_2CO_3$ or $Na_2CO_3$.

The crude product yield of the process according to the invention may, in the preparation of compounds of the general formula I, be greater than 70%, preferably greater than 85%, more preferably greater than 90%, even more preferably greater than 95%, based on the molar amount of the (haloorganyl)alkyl polyether silane used.

The crude product yield may be the gravimetrically determined sum of all isolated silane compounds after solvents and solids have been removed.

In the preparation of compounds of the general formula I, the amount of the $(X)(X')(X'')Si—(R^I)—S—(R^I)—Si(X)(X')(X'')$ formed as a by-product may be less than 50% by weight, preferably less than 15% by weight, more preferably less than 10% by weight, even more preferably less than 5% by weight, based on the amount of crude product.

The dry mercaptation reagents used in the preparation of compounds of the general formula I may be added to the reaction as solids or in solution.

The (haloorganyl)alkyl polyether silane, additives and solvents may be mixed with one another in any sequence, manner, temperature and duration, and only then can the dry mercaptation reagent be added.

The (haloorganyl)alkyl polyether silane, additives and the dry mercaptation reagent can be mixed with one another in any sequence, manner, temperature and duration, and only then can the solvent be added.

The dry mercaptation reagent, additives and the solvent can be mixed with one another in any sequence, manner, temperature and duration, and only then can the (haloorganyl)alkyl polyether silane be added.

The (haloorganyl)alkyl polyether silane, the solvent and the dry mercaptation reagent can be mixed with one another in any sequence, manner, temperature and duration and only then can the additives be added.

(Mercaptoorganyl)alkyl polyether silanes of the general formula I

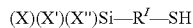   I can be prepared by reacting dry mercaptation reagents with (haloorganyl)alkyl polyether silane of the general formula II

   II and optionally additives and/or solvents, preferably in a closed vessel with exclusion of air and under elevated pressure.

It is possible, by virtue of the selection of the (haloorganyl) alkyl polyether silane, of the additives and of the solvent, to influence the composition of mixtures of compounds of the general formula I in an active and controlled manner.

The amount of hydrolyzable silicon halide in the (haloorganyl)alkyl polyether silane may be between 1 and 1000 mg/kg.

The amount of hydrolyzable silicon halide in the (haloorganyl)alkyl polyether silane may preferably be between 5 and 500 ppm, more preferably between 5 and 200 ppm, even more preferably between 10 and 50 ppm.

The amount of hydrolyzable silicon halide is determined by the following process:

Not more than 20 g of the sample are admixed in a 150 ml beaker with 80 ml of ethanol and 10 ml of acetic acid. The halide content is titrated potentiographically with silver nitrate solution (c(AgNO$_3$)=0.01 mol/l).

The process according to the invention can be carried out without solvent or in the presence of solvents.

The solvents used may be mixtures of solvents.

Solvents may be nonalcoholic solvents. The nonalcoholic solvents used may be alkanes, for example pentane, hexane, cyclohexane, heptane or octane, ethers, for example diethyl ether, tetrahydrofuran, 1,2-dimethoxyethane, dioxane, dioxolane, ethylene glycols or propylene glycols, aromatic solvents, for example benzene, toluene, o-xylene, m-xylene or p-xylene, or carbonyl-containing solvents, for example dimethylformamide.

Solvents may be compressed gases. Compressed gases may be in the liquid state, in the near-critical state or in the supercritical state. Compressed gases may be H$_2$S or NH$_3$.

Solvents may be alcohols. The alcohols used may be primary, secondary or tertiary alcohols having 1-24, preferably 1-4 and 12-24, more preferably 1-4 and 12-18, carbon atoms.

The primary, secondary or tertiary alcohols used may be methanol, ethanol, n-propanol, i-propanol, i-butanol, t-butanol, n-butanol, linear or branched dodecanol, n-tridecanol, i-tridecanol, linear or branched tetradecanol, linear or branched hexadecanol, or linear or branched octadecanol.

The alcohols used may be alkyl ether alcohols of the formula HO—(CR$^{III}_2$)—O-Alk$^I$ or HO—(CR$^{III}_2$)$_g$—O-Alk$^I$ or alkyl polyether alcohols of the formula HO—(CR$^{III}_2$)$_g$-Alk$^{II}$ or HO—(CR$^{III}_2$—CR$^{III}_2$—O)$_g$-Alk$^{II}$ where g=2-20, preferably 2-10, more preferably 3-6, R$^{III}$ are each independently H or an alkyl group, preferably CH$_3$ group, and Alk$^I$ and Alk$^{II}$ are each independently a branched or unbranched, saturated or unsaturated, aliphatic, aromatic or mixed aliphatic/aromatic monovalent C$_1$-C$_{35}$-hydrocarbon group, preferably C$_2$-C$_{25}$-hydrocarbon group, more preferably C$_3$-C$_{20}$-hydrocarbon group, even more preferably C$_6$-C$_{18}$-hydrocarbon group, exceptionally preferably C$_{11}$-C$_{18}$-hydrocarbon group.

The alkyl polyether alcohols used may be HO—(CH$_2$—CH$_2$—O)$_a$—C$_b$H$_{2b+1}$, where a is from 2 to 20, preferably 2-10, more preferably 2-8, even more preferably 3-6, and b=1-30, preferably 2-20, more preferably 6-18, even more preferably 10-18.

Alkyl polyether alcohols may be

HO—(CH$_2$—CH$_2$—O)$_2$—C$_6$H$_{13}$, HO—(CH$_2$—CH$_2$—O)$_3$—C$_6$H$_{13}$, HO—(CH$_2$—CH$_2$—O)$_4$—C$_6$H$_{13}$, HO—(CH$_2$—CH$_2$—O)$_5$—C$_6$H$_{13}$, HO—(CH$_2$—CH$_2$—O)$_6$—C$_6$H$_{13}$ HO—(CH$_2$—CH$_2$—O)$_7$—C$_6$H$_{13}$, HO—(CH$_2$—CH$_2$—O)$_8$—C$_6$H$_{13}$, HO—(CH$_2$—CH$_2$—O)$_9$—C$_6$H$_{13}$,

HO—(CH$_2$—CH$_2$—O)$_2$—C$_{10}$H$_{21}$, HO—(CH$_2$—CH$_2$—O)$_3$—C$_{10}$H$_{21}$, HO—(CH$_2$—CH$_2$—O)$_4$—C$_{10}$H$_{21}$, HO—(CH$_2$—CH$_2$—O)$_5$—C$_{10}$H$_{21}$, HO—(CH$_2$—CH$_2$—O)$_6$—C$_{10}$H$_{21}$, HO—(CH$_2$—CH$_2$—O)$_7$—C$_{10}$H$_{21}$, HO—(CH$_2$—CH$_2$—O)$_8$—C$_{10}$H$_{21}$, HO—(CH$_2$—CH$_2$—O)$_9$—C$_{10}$H$_{21}$,

HO—(CH$_2$—CH$_2$—O)$_2$—C$_{13}$H$_{27}$, HO—(CH$_2$—CH$_2$—O)$_3$—C$_{13}$H$_{27}$, HO—(CH$_2$—CH$_2$—O)$_4$—C$_{13}$H$_{27}$, HO—(CH$_2$—CH$_2$—O)$_5$—C$_{13}$H$_{27}$, HO—(CH$_2$—CH$_2$—O)$_6$—C$_{13}$H$_{27}$, HO—(CH$_2$—CH$_2$—O)$_7$—C$_{13}$H$_{27}$, HO—(CH$_2$—CH$_2$—O)$_8$—C$_{13}$H$_{27}$, HO—(CH$_2$—CH$_2$—O)$_9$—C$_{13}$H$_{27}$,

HO—(CH$_2$—CH$_2$—O)$_2$—C$_{15}$H$_{31}$, HO—(CH$_2$—CH$_2$—O)$_3$—C$_{15}$H$_{31}$, HO—(CH$_2$—CH$_2$—O)$_4$—C$_{15}$H$_{31}$, HO—(CH$_2$—CH$_2$—O)$_5$—C$_{15}$H$_{31}$, HO—(CH$_2$—CH$_2$—O)$_6$—C$_{15}$H$_{31}$, HO—(CH$_2$—CH$_2$—O)$_7$—C$_{15}$H$_{31}$, HO—(CH$_2$—CH$_2$—O)$_8$—C$_{15}$H$_{31}$ or HO—(CH$_2$—CH$_2$—O)$_9$—C$_{15}$H$_{31}$.

The alcohols used may be mixtures of alcohols.

The alcohols used may be mixtures of alkyl polyether alcohols.

When the solvent is an alcohol, a portion of the alcohol used as the solvent may be incorporated into the product of the general formula I during the mercaptation reaction, by transesterification on the silicon.

The amount of solvent may be at least 0.1% by weight, preferably from 10 to 1000% by weight, more preferably from 25 to 500% by weight, even more preferably from 50 to 200% by weight, of the haloorganyl(alkyl polyether silanes) used when the solvent is not a compressed gas.

In the case of use of solvents which are not compressed gases, elevated pressure may be understood to mean an increased pressure of from 0.1 to 50 bar, preferably from 0.5 to 25 bar, more preferably from 0.5 to 10 bar, exceptionally preferably from 0.5 to 6 bar, above standard pressure.

In the case of use of compressed gases, elevated pressure may be understood to mean an increased pressure of from 0.1 to 250 bar, preferably from 0.5 to 200 bar, more preferably from 1 to 150 bar, exceptionally preferably from 1 to 100 bar, above standard pressure.

The reaction can be effected at temperatures between 0 and 200° C., preferably between 50 and 150° C., more preferably between 60 and 125° C., exceptionally preferably between 70 and 110° C.

The reaction temperature and/or pressure optimal on the basis of the yield of target product and exploitation of the reaction volume may vary according to the structure of the (haloorganyl)alkyoxysilane used and of the solvent.

The reaction can be effected in a closed vessel under protective gas.

The reaction can be effected in corrosion-resistant or corrosion-prone reaction vessels or autoclaves.

The reaction can preferably be effected in corrosion-resistant reaction vessels or autoclaves, for example made of glass, Teflon, enamelled or coated steel, Hastelloy or tantalum.

The amount of by-products may, by virtue of selection of the reaction conditions, be less than 20 mol %, preferably less than 15 mol %, more preferably less than 10 mol %, based on the (haloorganyl)alkyl polyether silane used.

In addition to the desired mercaptoorganylsilane compounds, the by-products formed may be the corresponding monosulfates, and also, depending on the structure of the monomeric mercaptoorganylsilane compound, various combinations of dimeric or oligomeric siloxanes formed from products or else products with reactants.

One advantage of the process according to the invention is the high conversions with short batch times and temperatures realizable in a technically simple manner.

EXAMPLES

The dried NaSH used is the commercial product from STREM/ABCR (water content: 0.1% by weight determined by the method described above).

The $H_2S$ used (purity 99.5%+) is purchased in a gas bottle from Aldrich.

The starting compounds $Cl-CH_2-CH_2-CH_2-Si(O-C_2H_5)[(O-CH_2-CH_2)_5-O-C_{13}H_{27}]_2$, $Cl-CH_2-CH_2-CH_2-Si(O-C_2H_5)_2[(O-CH_2-CH_2)_5-O-C_{13}H_{27}]$, $Cl-CH_2-CH_2-CH_2-Si(O-C_2H_5)_2[(O-CH_2-CH_2)_{10}-O-C_{13}H_{27}]$, $Cl-CH_2-CH_2-CH_2-Si(O-C_2H_5)_2[(O-CH_2-CH_2)_{18}-O-C_{13}H_{27}]$, $Cl-CH_2-CH_2-CH_2-Si(O-Et)[(O-CH_2-CH_2)-O-C_4H_9]_2$ and $Cl-CH_2-CH_2-CH_2-Si(O-Et)[(O-CH_2-CH_2)_2-O-C_2H_5]_2$ are prepared analogously to the process described in DE 102006027235.8 by catalyzed transesterification from the chloropropyl(triethoxysilanes) and the corresponding (polyether)monoalkyl alcohols.

Example 1

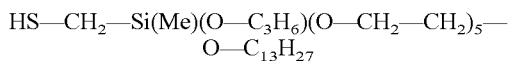

A Buechi glass autoclave is initially charged with 300 ml of dry i-propanol (Seccosolv) and 37.1 g of dry NaSH (ex STREM). 6.3 g of glacial acetic acid are added to the mixture and the autoclave is closed. 471.6 g of $Cl-CH_2-Si(Me)[(O-CH_2-CH_2)_5-O-C_{13}H_{27}]_2$ are added to the autoclave with a pump at 50° C. within 40 min. The suspension is stirred at 80° C. for 180 min. The solid present in the suspension is filtered off and washed with 50 ml of i-propanol. The filtrate is concentrated on a rotary evaporator. After the end filtration, 435.9 g of product are obtained.

The $^{13}C$ NMR analysis of the resulting product shows, based on the silane compounds, the following average composition:

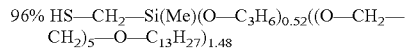

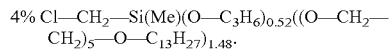

The polyether alcohol $H-(O-CH_2-CH_2)_g-O-C_{13}H_{27}$ released in the transesterification is detectable in the $^{13}C$ NMR spectrum.

Example 2

$HS-CH_2-Si(O-Et)_{0.33}(O-C_3H_7)_{1.56}[(O-CH_2-CH_2)_5-O-C_{13}H_{27}]_{1.1}$

A Buechi glass autoclave is initially charged with 300 ml of dry i-propanol (Seccosolv) and 37.5 g of dry NaSH (ex STREM). 6.3 g of glacial acetic acid are added to the mixture and the autoclave is closed. 283.5 g of $Cl-CH_2-Si(OEt)_2[(O-CH_2-CH_2)_5-O-C_{13}H_{27}]$ are added to the autoclave with a pump at 50° C. within 40 min. The suspension is stirred at 80° C. for 180 min. The solid present in the suspension is filtered off. The filtrate is concentrated on a rotary evaporator. After the end filtration, 203.3 g of product are obtained.

The $^{13}C$ NMR analysis of the resulting product shows, based on the silane compounds, the following averaged composition

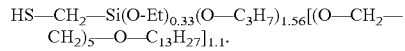

The substitution of the Cl function with an HS function proceeds quantitatively according to the results of the NMR analyses.

Example 3

Reaction of $Cl-CH_2-CH_2-CH_2-Si(O-C_2H_5)[(O-CH_2-CH_2)_5-O-C_{13}H_{27}]_2$

A Buechi glass autoclave is initially charged with 97 g of dry i-propanol (Seccosolv) and 7.6 g of dried NaSH. 145 g of $Cl-CH_2-CH_2-CH_2-Si(O-C_2H_5)[(O-CH_2-CH_2)_5-O-C_{13}H_{27}]_2$ are added to the autoclave with a pump. The suspension and the autoclave are purged with $H_2S$ for 15 min, then the autoclave is closed and adjusted to 1 bar gauge with $H_2S$. The suspension is stirred at 50° C. for 30 min and then at 85° C. for 300 min. The resulting suspension is transferred to a flask, freed of the solvent by distillation and filtered. 136.7 g of product are obtained, which corresponds to 94.3% of theory.

The $^1H$ NMR analysis of the resulting product shows that 100% of the Cl functions have been converted to HS functions, and 4% of these to further oxidation products with $S_2$ functions.

The polyether alcohol $H-(O-CH_2-CH_2)_5-O-C_{13}H_{27}$ released in the esterification with i-propanol which takes place is detectable in the $^{13}C$ NMR spectrum.

Example 4

$HS-CH_2-CH_2-CH_2-Si(O-Et)[(O-CH_2-CH_2)_5-O-C_{13}H_{27}]_2$

A Buechi glass autoclave is initially charged with 15.6 g of dried NaSH, and 300 g of $Cl-CH_2-CH_2-CH_2-Si(O-$ $C_2H_5)[(O-CH_2-CH_2)_5-O-C_{13}H_{27}]_2$ are added thereto with a pump. The suspension and the autoclave are purged with $H_2S$ for 15 min, then the autoclave is closed and adjusted to 1 bar gauge with $H_2S$. The suspension is stirred at 50° C. for 30 min and at 110-120° C. for 300 min. The resulting suspension is filtered, transferred to a flask and freed of volatile constituents at 80° C. under reduced pressure for 30 min. 276.6 g of product are obtained, which corresponds to 92.6% of theory.

The $^1H$ NMR analysis of the resulting product shows that 100% of the Cl functions have been converted to HS functions and 5.2% of them have been converted to further oxidation products with $S_2$ functions.

The transesterification distribution on the silicon remains intact in the reaction and, according to NMR analyses, corresponds to that of the starting material $Cl-CH_2-CH_2-CH_2-Si(O-C_2H_5)[(O-CH_2-CH_2)_5-O-C_{13}H_{27}]_2$.

Example 5

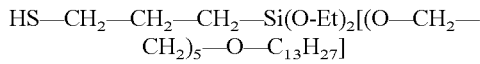

A Buechi glass autoclave is initially charged with 15.6 g of dried NaSH, and 200 g of $Cl-CH_2-CH_2-CH_2-Si(O-C_2H_5)_2[(O-CH_2-CH_2)_5-O-C_{13}H_{27}]$ are added thereto with a pump. The suspension and the autoclave are purged with $H_2S$ for 15 min, and then the autoclave is closed. The suspension is stirred at 75° C. for 30 min and then at 110-120° C. for 300 min. The resulting suspension is filtered and transferred to a flask. 185.2 g of product are obtained, which corresponds to 92.9% of theory.

Example 6

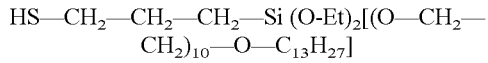

A Buechi glass autoclave is initially charged with 15.6 g of dried NaSH, and 257 g of $Cl-CH_2-CH_2-CH_2-Si(O-C_2H_5)_2[(O-CH_2-CH_2)_{10}-O-C_{13}H_{27}]$ are added thereto with a pump. The suspension and the autoclave are purged with $H_2S$ for 15 min, and then the autoclave is closed. The suspension is stirred at 50° C. for 30 min and then at 110-120° C. for 300 min. The resulting suspension is filtered and transferred to a flask. 246.7 g of product are obtained, which corresponds to 96.2% of theory.

Example 7

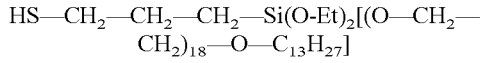

A Buechi glass autoclave is initially charged with 15.6 g of dried NaSH, and 350 g of $Cl-CH_2-CH_2-CH_2-Si(O-C_2H_5)_2[(O-CH_2-CH_2)_{18}-O-C_{13}H_{27}]$ are added thereto with a pump. The suspension and the autoclave are purged with $H_2S$ for 15 min, and then the autoclave is closed. The suspension is stirred at 50° C. for 30 min and then at 110-120° C. for 300 min. The resulting suspension is filtered and transferred to a flask. 336.4 g of product are obtained, which corresponds to 96.3% of theory.

Example 8

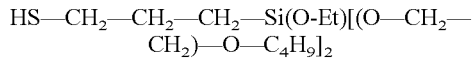

A Buechi glass autoclave is initially charged with 15.6 g of dried NaSH, and 101.5 g of $Cl-CH_2-CH_2-CH_2-Si(O-Et)[(O-CH_2-CH_2)-O-C_4H_9]_2$ are added thereto with a pump. The suspension and the autoclave are purged with $H_2S$ for 15 min, and then the autoclave is closed. The suspension is stirred at 50° C. for 30 min and then at 110-120° C. for 300 min. The resulting suspension is filtered and transferred to a flask. 93.6 g of product are obtained, which corresponds to 92.8% of theory.

According to $^1H$ NMR analyses, only 22% of all Cl-propyl functions have been converted to HS-propyl functions.

The transesterification distribution on the silicon is unchanged compared to the starting material $Cl-CH_2-CH_2-CH_2-Si(O-Et)[(O-CH_2-CH_2)-O-C_4H_9]_2$ according to NMR analyses.

Example 9

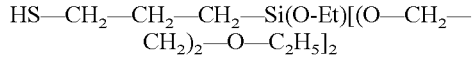

A Buechi glass autoclave is initially charged with 15.6 g of dried NaSH, and 110 g of $Cl-CH_2-CH_2-CH_2-Si(O-Et)[(O-CH_2-CH_2)_2-O-C_2H_5]_2$ are added thereto with a pump. The suspension and the autoclave are purged with $H_2S$ for 15 min and then the autoclave is closed. The suspension is stirred at 50° C. for 30 min and then at 110-120° C. for 300 min. The resulting suspension is filtered and transferred to a flask. 98 g of product are obtained, which corresponds to 90.8% of theory.

According to $^1H$ NMR analyses, only 63% of all Cl-propyl functions have been converted to HS-propyl functions.

The transesterification distribution on the silicon is unchanged compared to the starting material $Cl-CH_2-CH_2-CH_2-Si(O-Et)[(O-CH_2-CH_2)_2-O-C_2H_5]_2$ according to NMR analyses.

The invention claimed is:

1. A process for preparing a (mercaptoorganyl)alkyl polyether silane, comprising reacting a dry mercaptation reagent with a (haloorganyl)alkyl polyether silane, wherein said mercaptation reagent has a water content of less than 3% by weight.

2. The process of claim 1, wherein the reaction between said dry mercaptation reagent and said (haloorganyl)alkyl polyether silane is carried out in a closed vessel, in the absence of air and under an elevated pressure.

3. The process of claim 1, wherein the reaction between said dry mercaptation reagent and said (haloorganyl)alkyl polyether silane is carried out in a solvent consisting of one or more organic solvents or one or more compressed gases.

4. The process of claim 1, wherein said (mercaptoorganyl) alkyl polyether silane is a compound of formula I:

wherein:

X is an alkyl polyether group $O-(CR^H_2)_w-O-)_v$Alk where v=1-40, w=1-40, $R^H$ are each independently H, a phenyl group or an alkyl group, Alk is a branched or unbranched, saturated or unsaturated, substituted or unsubstituted, aliphatic, aromatic or mixed aliphatic/aromatic monovalent $C_1$-$C_{35}$-hydrocarbon group, X' is a branched or unbranched alkyl, a branched or unbranched alkoxy, a branched or unbranched alkenyloxy group, a branched or unbranched aryloxy group, a branched or unbranched alkylaryloxy group, a branched or unbranched aralkyloxy group or an X group, X" is a branched or unbranched alkyl, a branched or unbranched alkoxy, a branched or unbranched alkenyloxy group, a branched or unbranched aryloxy group, a branched or unbranched alkylaryloxy group, a branched or unbranched aralkyloxy group or an X group, $R^I$ is a branched or unbranched, saturated or unsaturated, aliphatic, aromatic or mixed aliphatic/aromatic divalent $C_1$-$C_{30}$ hydrocarbon group.

5. The process of claim 1, wherein said (haloorganyl)alkyl polyether silane is a compound of formula II:

(X)(X')(X")Si—$R^I$-Hal  (II)

where $R^I$, X, X' and X" are each as defined as for formula I, and Hal is chlorine, bromine, fluorine or iodine.

6. The process of claim 1, wherein said dry mercaptation reagent is an alkali metal hydrogensulfide or ammonium hydrogensulfide.

7. The process of claim 1, wherein said dry mercaptation reagent is selected from the group consisting of: lithium hydrogensulfide (LiSH), sodium hydrogensulfide (NaSH), potassium hydrogensulfide (KSH) and cesium hydrogensulfide (CsSH).

8. The process of claim 1, wherein said dry mercaptation reagent is (NH$_4$)SH, NH$_3$(Sub)SH, NH$_2$(Sub)$_2$SH or NH(Sub)$_3$SH, wherein Sub is a branched or unbranched, saturated or unsaturated, aliphatic, aromatic or mixed aliphatic/aromatic monovalent $C_1$-$C_{30}$ hydrocarbon group.

9. The process of claim 1, wherein additives are added to the reaction mixture at the start of the reaction and/or during the reaction and/or at the end of the reaction.

10. The process of claim 1, wherein the molar amount of dry mercaptation reagent used is from 70 mol % to 150 mol % of the molar amount of the (haloorganyl)alkyl polyether silane used.

11. The process of claim 3, wherein said solvent comprises one or more compounds selected from the group consisting of: an alkane; ether; aromatic solvent; alcohol or carbonyl-containing solvent.

12. The process of claim 4, wherein said (haloorganyl)alkyl polyether silane is a compound of formula II:

(X)(X')(X")Si—$R^I$-Hal  (II)

where $R^I$, X, X' and X" are each as defined as for formula I, and Hal is chlorine, bromine, fluorine or iodine.

13. The process of claim 12, wherein the reaction between said dry mercaptation reagent and said (haloorganyl)alkyl polyether silane is carried out in a closed vessel, in the absence of air and under an elevated pressure.

14. The process of claim 13, wherein the reaction between said dry mercaptation reagent and said (haloorganyl)alkyl polyether silane is carried out in a solvent consisting of one or more organic solvents or one or more compressed gases.

15. The process of claim 14, wherein said dry mercaptation reagent is an alkali metal hydrogensulfide or ammonium hydrogensulfide.

16. The process of claim 14, wherein said dry mercaptation reagent is selected from the group consisting of: lithium hydrogensulfide (LiSH), sodium hydrogensulfide (NaSH), potassium hydrogensulfide (KSH) and cesium hydrogensulfide (CsSH).

17. The process of claim 14, wherein said dry mercaptation reagent is (NH$_4$)SH, NH$_3$(Sub)SH, NH$_2$(Sub)$_2$SH or NH(Sub)$_3$SH, wherein Sub is a branched or unbranched, saturated or unsaturated, aliphatic, aromatic or mixed aliphatic/aromatic monovalent $C_1$-$C_{30}$ hydrocarbon group.

18. The process of claim 14, wherein additives are added to the reaction mixture at the start of the reaction and/or during the reaction and/or at the end of the reaction.

19. The process of claim 14, wherein the molar amount of dry mercaptation reagent used is from 70 mol % to 150 mol % of the molar amount of the (haloorganyl)alkyl polyether silane used.

20. The process of claim 14, wherein:
a) said dry mercaptation reagent is selected from the group consisting of: lithium hydrogensulfide (LiSH), sodium hydrogensulfide (NaSH), potassium hydrogensulfide (KSH) and cesium hydrogensulfide (CsSH);
b) additives are added to the reaction mixture at the start of the reaction and/or during the reaction and/or at the end of the reaction; and
c) the molar amount of dry mercaptation reagent used is from 70 mol % to 150 mol % of the molar amount of the (haloorganyl)alkyl polyether silane used.

* * * * *